United States Patent [19]

Nudelman et al.

[11] Patent Number: 5,421,733
[45] Date of Patent: Jun. 6, 1995

[54] SYNTHESIS OF LE$^x$; DIMERIC LE$^x$ (DIFUCOSYL Y$_2$; III$^3$FUCV$^3$FUCNLC$_6$CER); SIALYLATED FORMS THEREOF; AND ANALOGUES THEREOF

[75] Inventors: Edward Nudelman; Khalid K. Sadozai; Henrik Clausen; Sen-itiroh Hakomori; Mark Stroud, all of Seattle, Wash.

[73] Assignee: The Biomembrane Institute, Seattle, Wash.

[21] Appl. No.: 705,671

[22] Filed: May 24, 1991
(Under 37 CFR 1.47)

Related U.S. Application Data

[63] Continuation-in-part of Ser. No. 344,628, Apr. 28, 1989, abandoned.

[51] Int. Cl.$^6$ ............................................. C12P 19/02
[52] U.S. Cl. ................................. 435/105; 435/101; 435/193; 435/97; 435/74
[58] Field of Search ................. 435/101, 193, 97, 74, 435/105

[56] References Cited

U.S. PATENT DOCUMENTS

| | | | |
|---|---|---|---|
| 4,876,199 | 10/1989 | Hakomori | 435/948 |
| 4,904,596 | 2/1990 | Hakomori | 435/948 |
| 5,030,723 | 7/1991 | Nudelman et al. | 536/55.1 |

OTHER PUBLICATIONS

Hakomori et al., *J. Biol. Chem.*, vol. 258 (19), Oct. 1983, pp. 11819–11822.

Fukushi et al., *J. Biol. Chem*, vol. 259 (16), Aug. 1984, pp. 10511–10517.

Hakomori et al., *J. Biol. Chem.*, vol. 259 (7), Apr. 1984, pp. 4672–4680.

*Primary Examiner*—Ronald W. Griffin
*Assistant Examiner*—Pamela S. Webber
*Attorney, Agent, or Firm*—Sughrue, Mion, Zinn, Macpeak & Seas

[57] ABSTRACT

A process for preparing difucosyl Y$_2$ antigen (dimeric Le$^x$), said process comprising: (1) preparing a lactonorhexaosylceramide backbone or a lactonorhexaosylsaccharide backbone linked to a carrier molecule; and (2) enzymatically fucosylating said backbone at the III$^3$ and V$^3$ positions through an $\alpha 1 \rightarrow 3$ linkage. A process for preparing Le$^y$ antigen analogues, said process comprising: (1) preparing a lactonorhexaosyl-ceramide backbone or a lactonorhexaosylsaccharide backbone linked to a carrier molecule; and (2) enzymatically fucosylating said backbone at the terminal $\beta$-Gal through an $\alpha 1 \rightarrow 2$ linkage; and (3) enzymatically fucosylating said backbone at one or more positions through an $\alpha 1 \rightarrow 3$ linkage, provided that steps (2) and (3) can be conducted simultaneously or in any order. A process for preparing a fucosylated lactonorhexaosylceramide, lactonorhexaosylsaccharide linked to a carrier molecule or higher analogues thereof, said process comprising: (1) preparing a lactonorhexaosylceramide backbone, a lactonorhexaosylsaccharide backbone linked to a carrier molecule or backbones of higher analogues thereof; and (2) enzymatically fucosylating one or more residues of said backbone. A process for preparing sialyl Le$^x$ and sialyl dimeric Le$^x$.

10 Claims, 19 Drawing Sheets

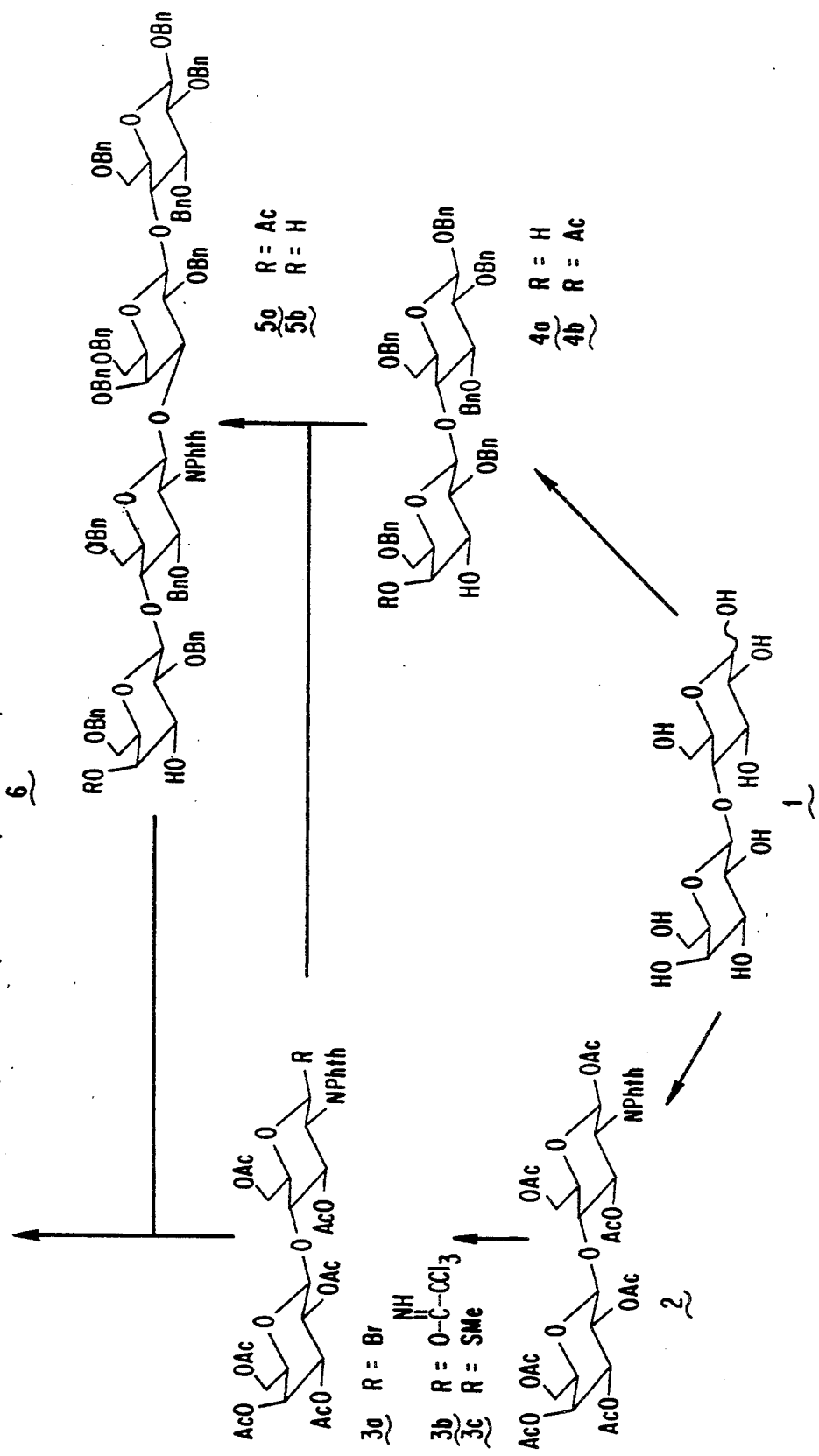
FIG. 1A. Synthetic Plan for Lactonorhexaosyl (Structure 6) by a Stepwise Approach (Mode I)
Gal β1→4 Glc NAc β1→3 Gal β1→4 Glc β1→4 Gal β1→3 Gal β1→4 Glc

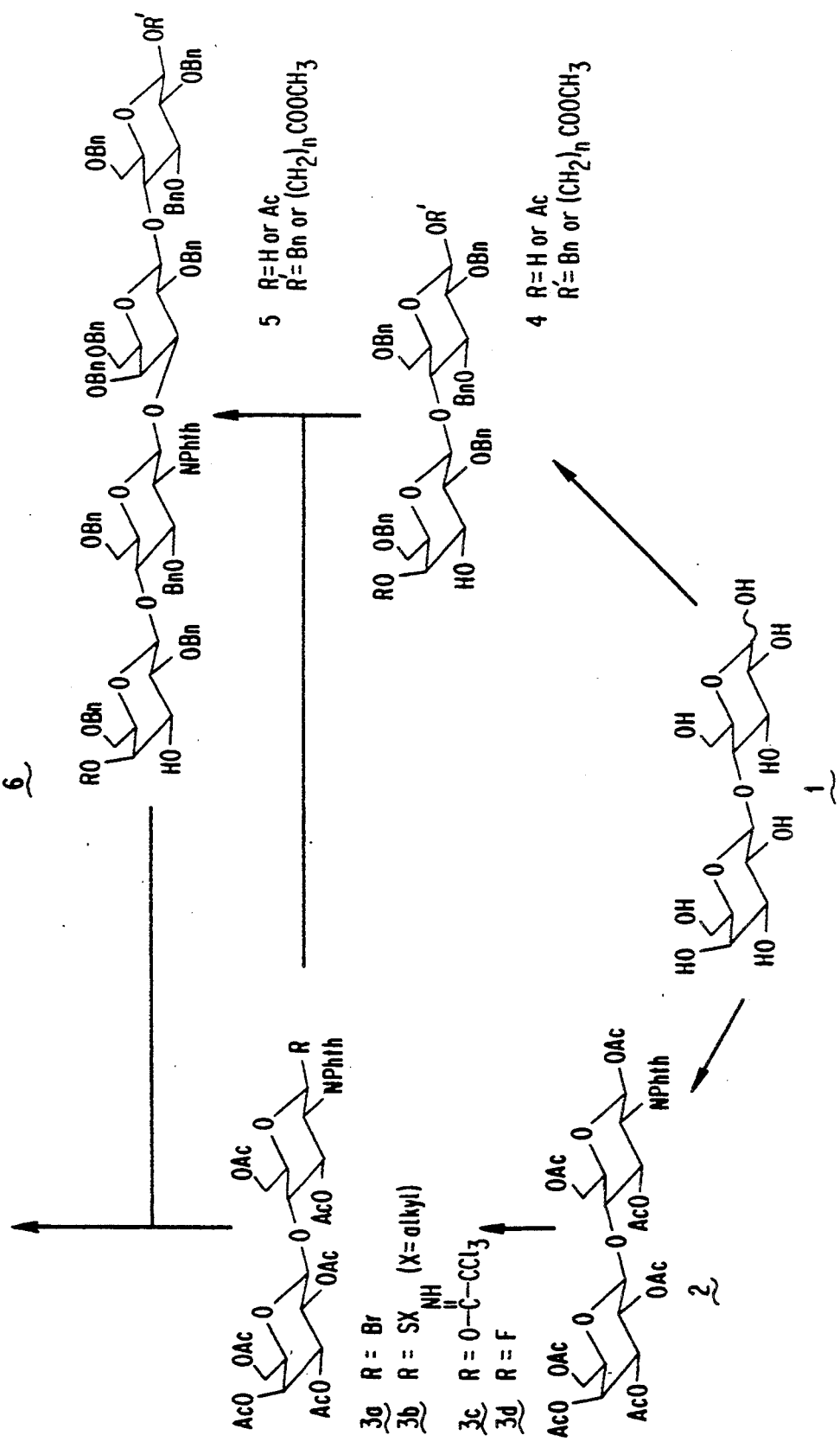
FIG. 1B Synthetic Plan for Lactonorhexaosyl (Structure 6) by a Stepwise Approach (Mode I)

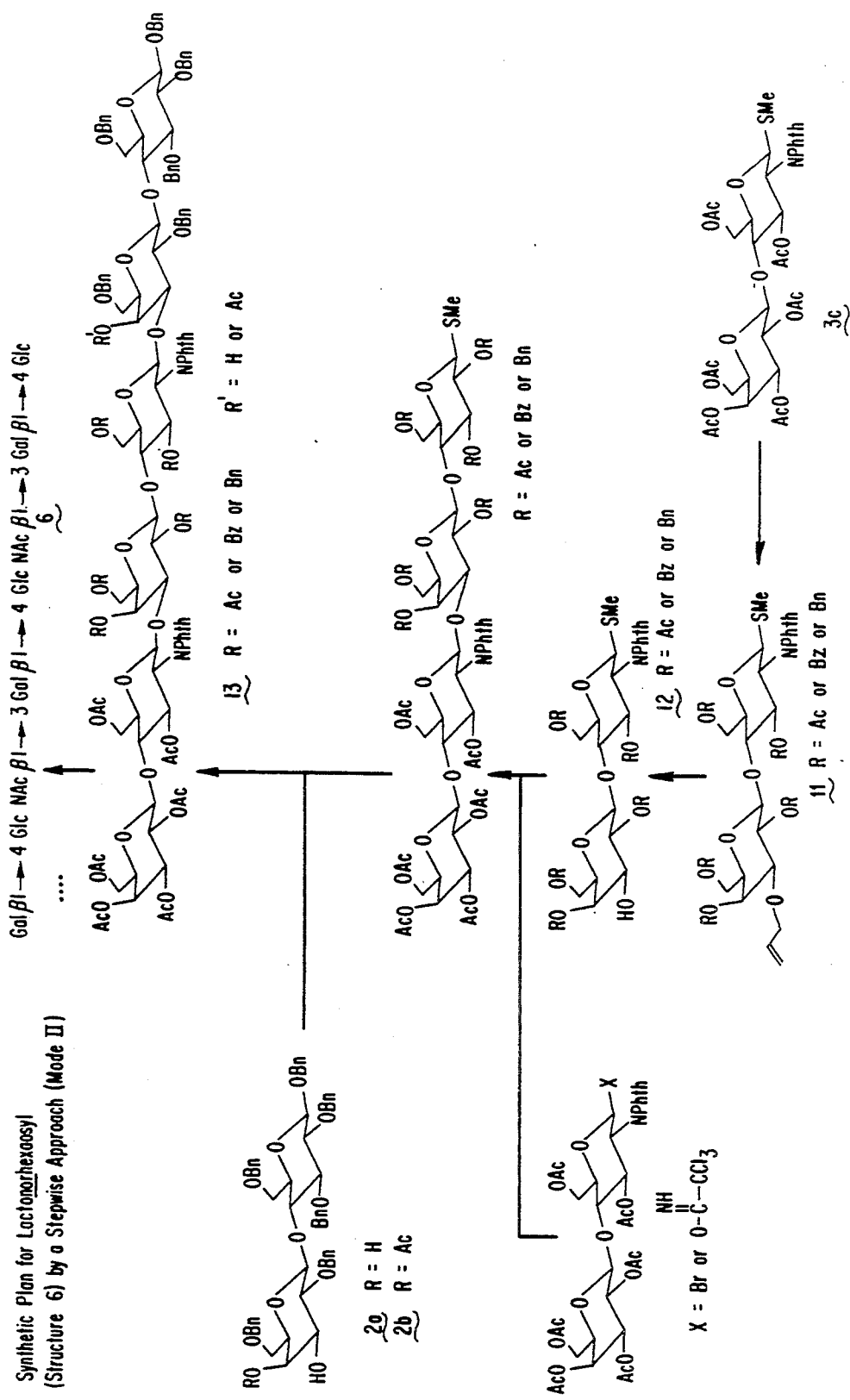
FIG. 2A  Synthetic Plan for Lactonorhexaosyl (Structure 6) by a Stepwise Approach (Mode II)

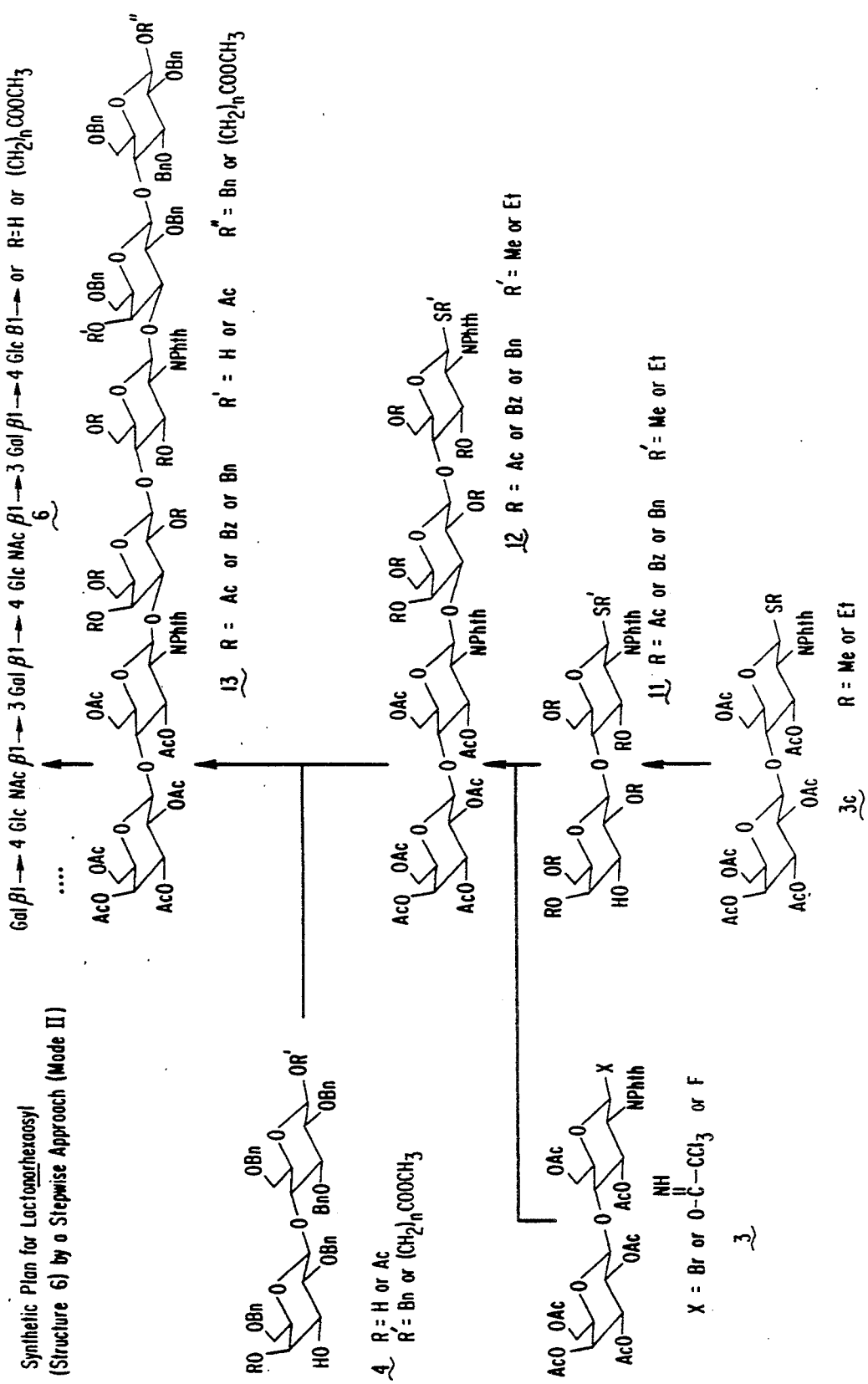
FIG. 2B Synthetic Plan for Lactonorhexaosyl (Structure 6) by a Stepwise Approach (Mode II)

Synthesis of Lactosaminyl donors

Synthesis of Lactosaminyl donors

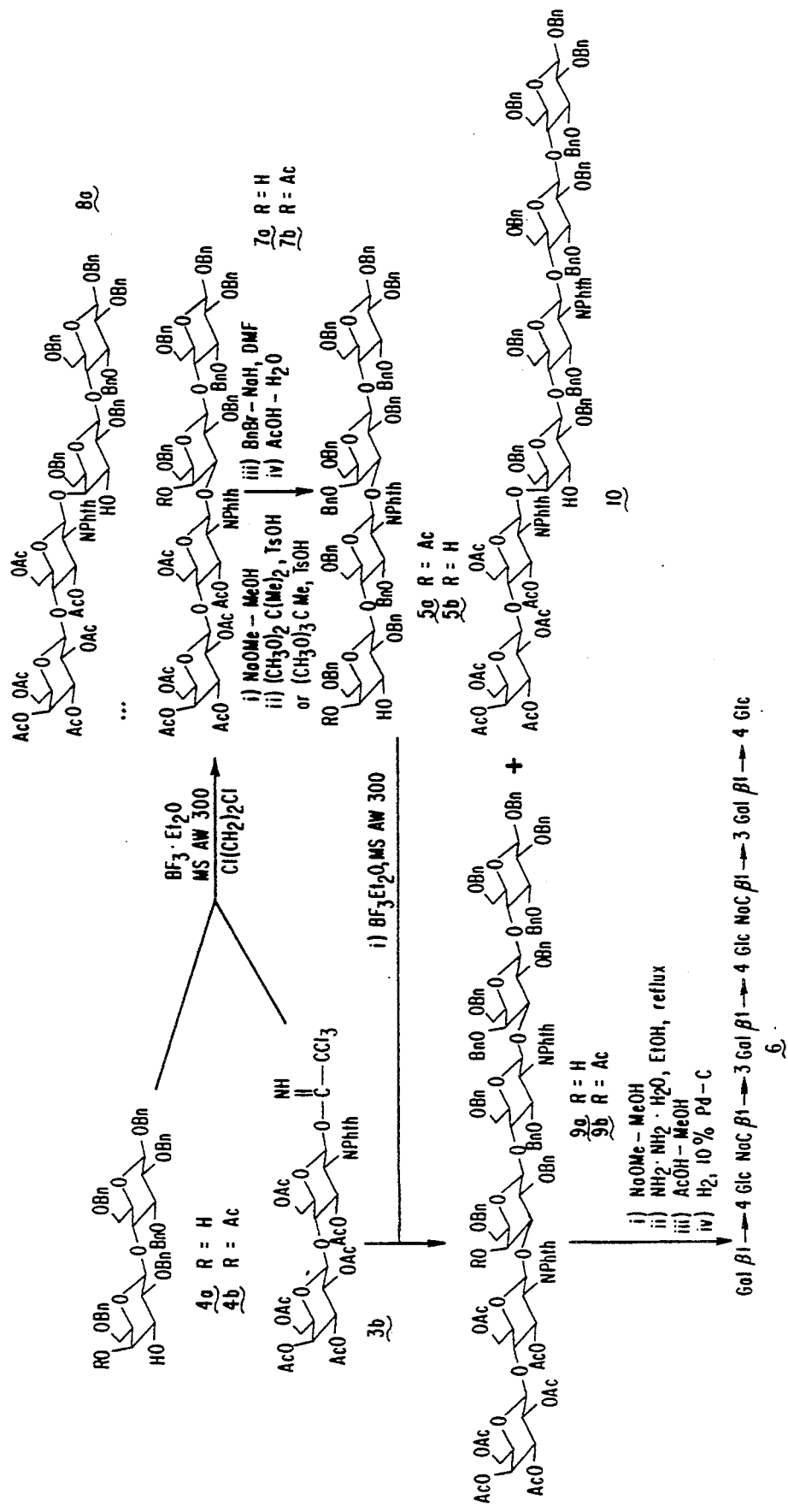
FIG. 6 Synthesis of Lactonorhexosyl (Structure 6)

1 2 3 4 5 6

1 2 3 4 5 6

1 2 3 4 5 6

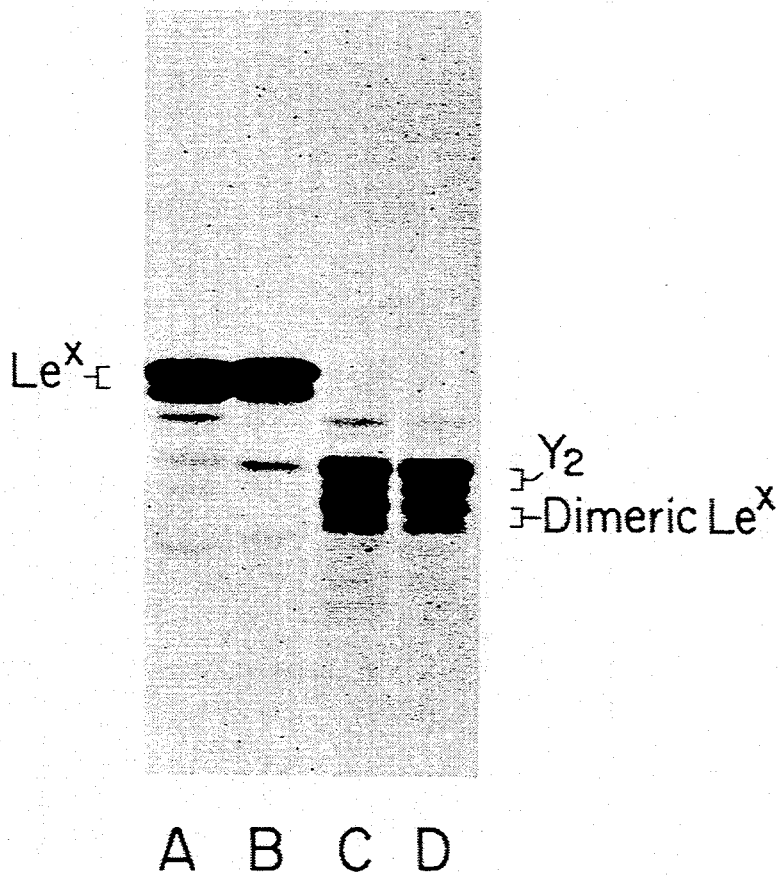

1 2 3 4 5   1 2 3 4 5   1 2 3 4 5

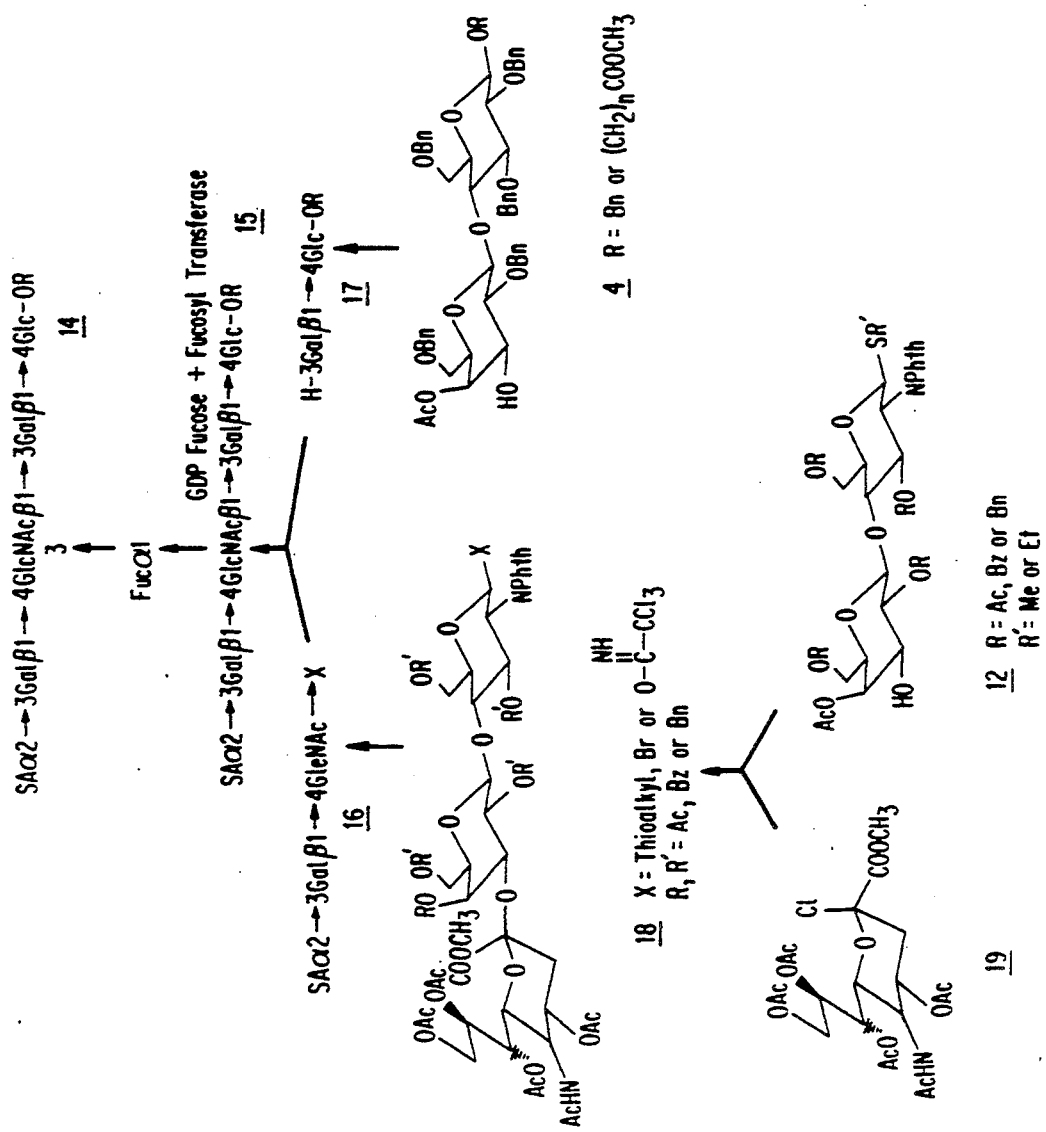
FIG. 11 Synthetic Plan for Sialyl Le$^x$

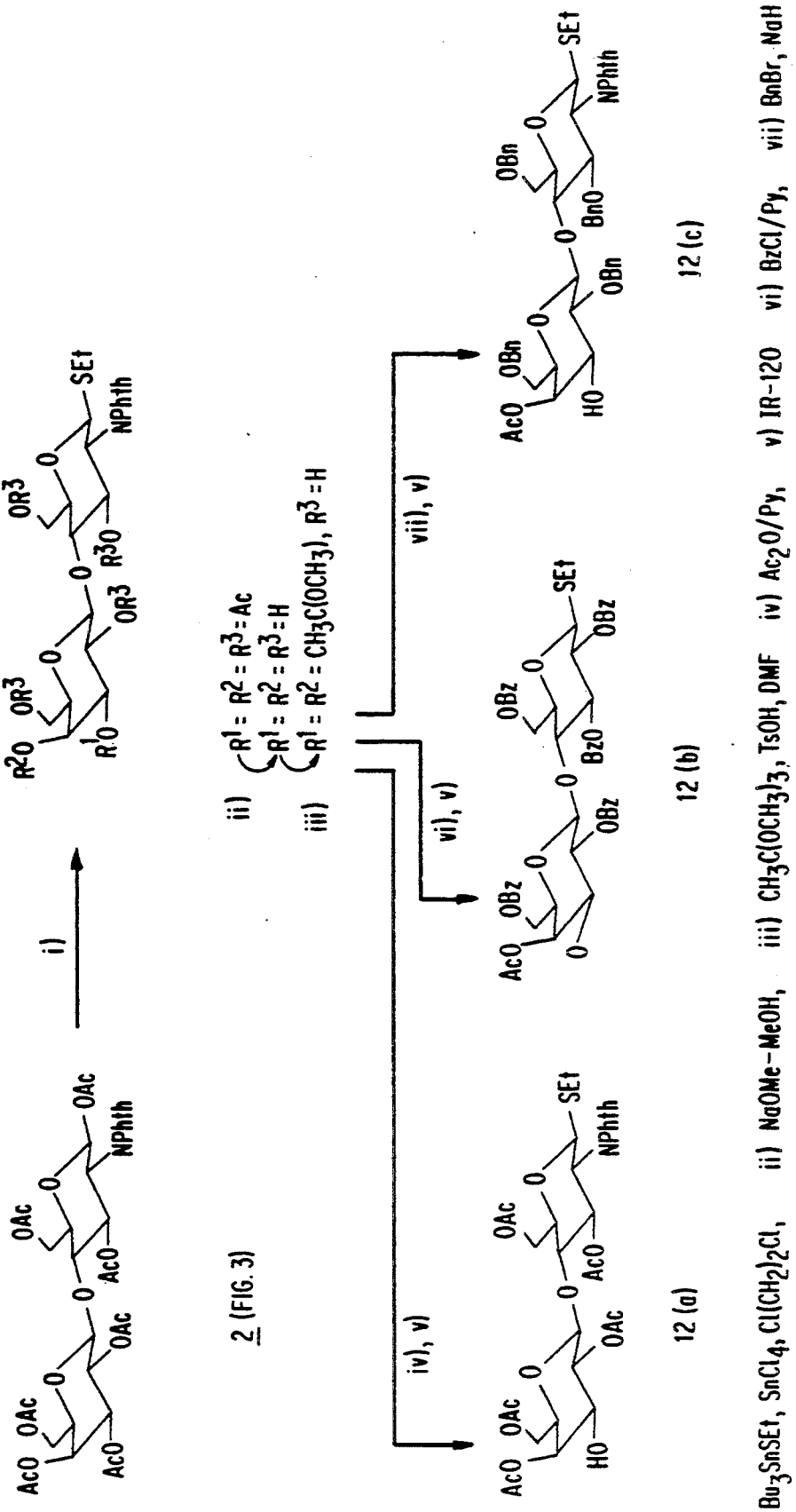
FIG. 12 Synthesis of Lactosaminyl Acceptor (12)
i) Bu₃SnSEt, SnCl₄, Cl(CH₂)₂Cl, ii) NaOMe-MeOH, iii) CH₃C(OCH₃)₃, TsOH, DMF iv) Ac₂O/Py, v) IR-120 vi) BzCl/Py, vii) BnBr, NaH

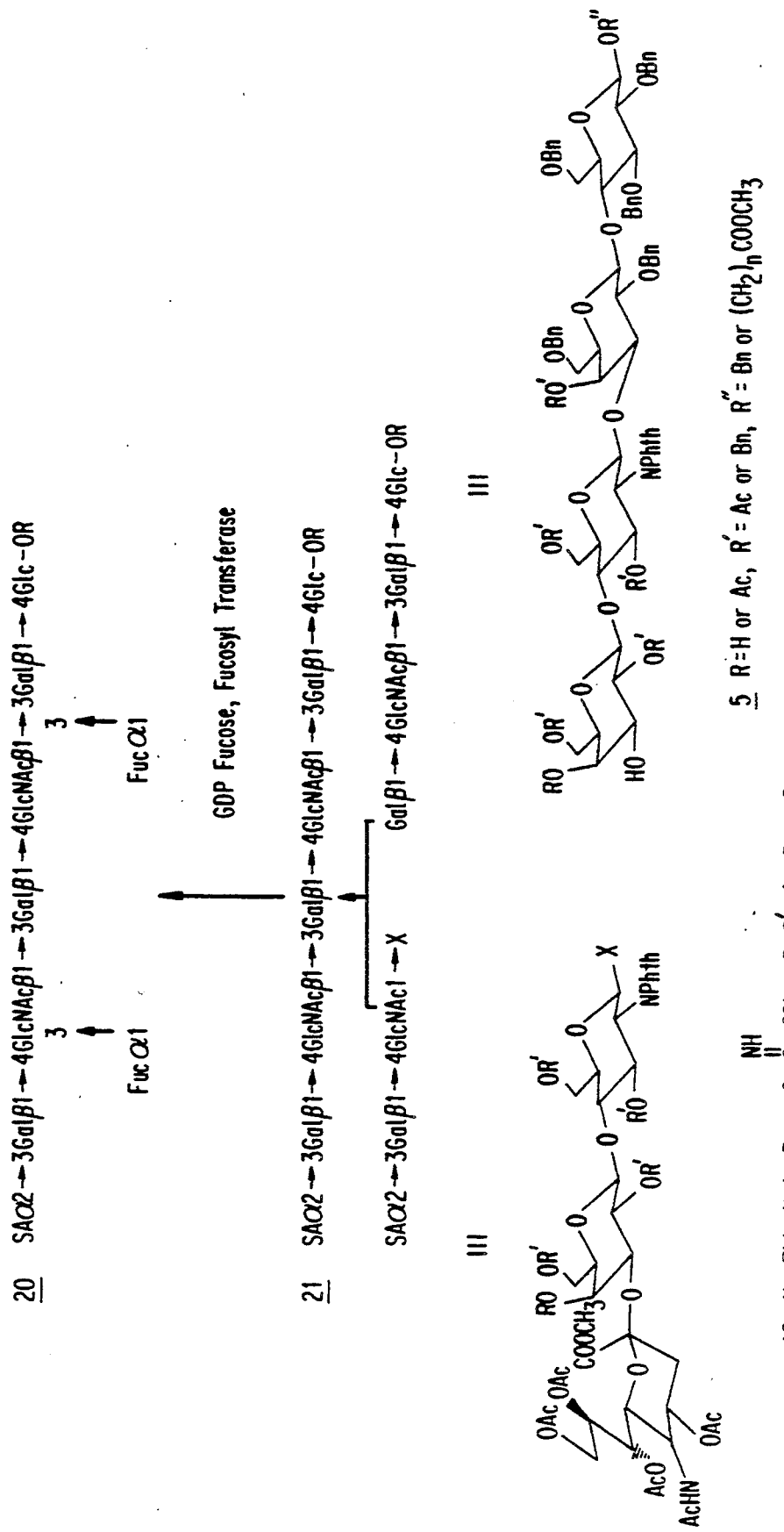
FIG. 13 Synthetic Plan for Sialyl Dimeric Le$^x$

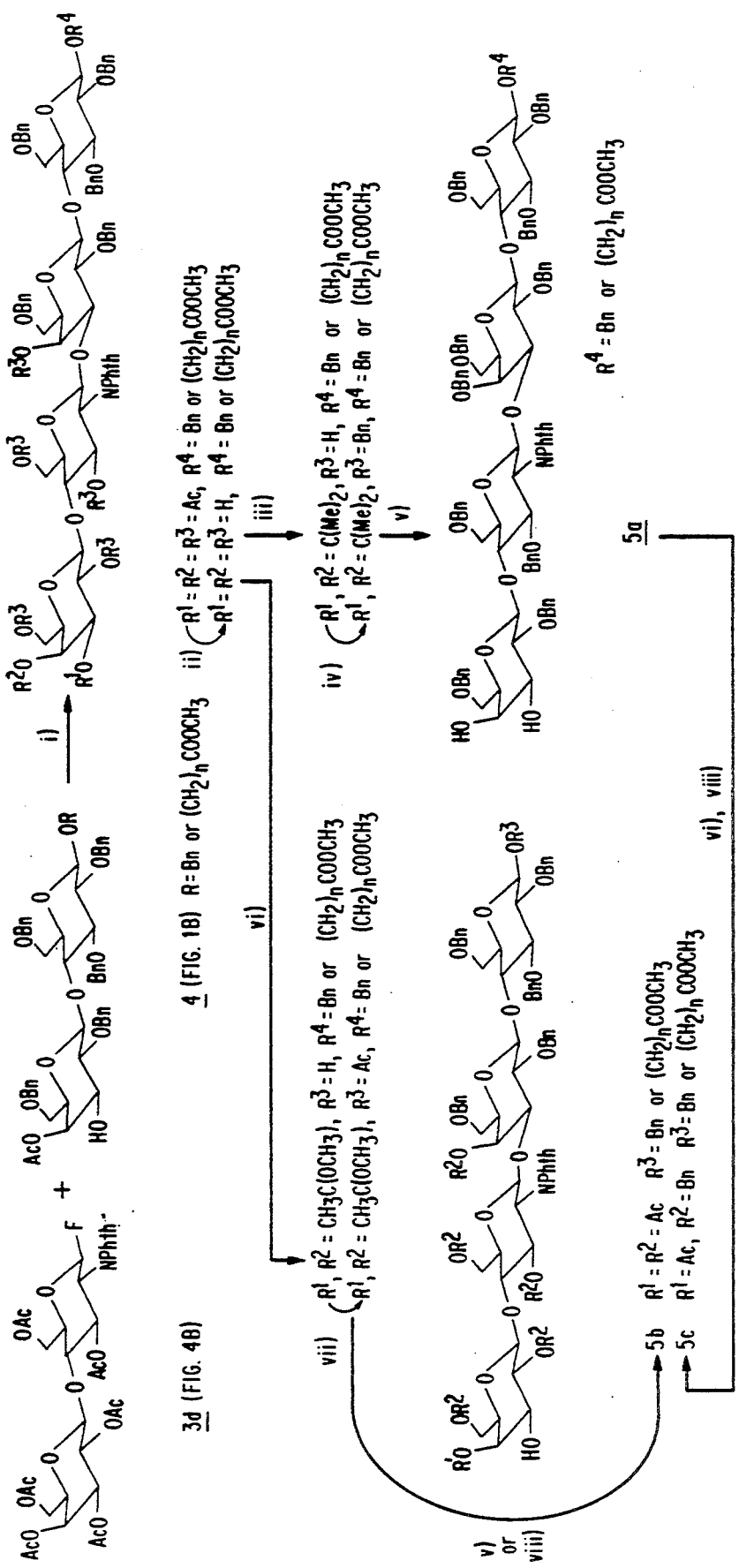

SYNTHESIS OF LE$^x$; DIMERIC LE$^x$ (DIFUCOSYL Y$_2$; III$^3$FUCV$^3$FUCNLC$_6$CER); SIALYLATED FORMS THEREOF; AND ANALOGUES THEREOF

This is a continuation-in-part of U.S. application Ser. No. 07/344,628, filed on 28 Apr. 1989, now abandoned.

FIELD OF THE INVENTION

The present invention relates to a process for synthesizing Le$^x$, dimeric Le$^x$ (i.e., difucosyl Y$_2$; III$_3$FucV$_3$FucnLc$_6$Cer), higher analogues thereof and sialylated forms thereof. Di- and trimeric Le$^x$ are especially important tumor antigens and are useful for developing vaccines against human cancer and specific effectors to dampen inflammatory processes of rheumatoid arthritis.

More particularly, the invention relates to a process for the synthesis of di- and trifucosyl Le$^x$, higher analogues thereof and sialylated forms thereof by means of a one-step reaction which results in unexpectedly superior yields.

The present invention also relates to a process for synthesis of Le$^y$ antigen analogues by means of a one-step reaction which results in unexpectedly superior yields.

BACKGROUND OF THE INVENTION

The glycolipids dimeric Le$^x$(difucosyl Y$_2$; III$^3$FucV$^3$FucnLc$_6$Cer) and trimeric Le$^x$ (III$^3$FucV$^3$FucVII$^3$FucnLc$_8$Cer) are major antigens that are found in various human adenocarcinomas but are absent in corresponding normal tissue (Hakomori et al., 1984, *J. Biol. Chem.*, 259, 4672-2680). A monoclonal antibody directed to those structures, but not cross-reacting with simple Le$^x$ (see Table I), is an important reagent for detecting the presence of the antigens in tumor cells (Fukushi et al., 1984, *J. Biol. Chem.*, 259, 4681-4685; Fukushi et al., 1984, *J. Exp. Med.*, 159, 506-520) and in sera of patients with cancer. The antibody, however, reacts on immunohistochemistry or immunofluorescence with selected normal cells, such as epithelial cells of proximal convoluted tubules of kidney and weakly with some subpopulations of granulocytes (Fukushi et al., 1984, *Cancer Res.*, 45, 3711-1717).

More recently, the antibody was found to react with granulocytes of inflammatory bone marrow adjacent to joints affected with rheumatoid arthritis (RA) (Ochi et al, 1988, *J. Rheumatol.*, 15, 1609-1615). Intradermal inoculation of liposomes containing the glycolipids suppresses the appearance of inflammatory granulocytes in the bone marrow of RA-affected joints with a subsequent reduction of RA symptoms.

Because of the presence of the antigens in high concentration in various types of human cancer and inflammatory processes, the antigens are expected to be useful components for developing anti-cancer and anti-inflammatory vaccines. To support this idea, reconstituted Newcastle's Disease virus membrane including the dimeric Le$^x$ antigen induced an immune response that suppressed growth of murine tumors bearing Le$^x$.

Le$^y$ antigens, including extended Le$^y$ (Le$^y$ octasaccharide ceramide) and trifucosyl Le$^y$, are also important human cancer antigens and are expected to be useful components for developing anti-cancer vaccines.

Thus the demand for Le$^x$ dimeric Le$^x$ and sialylated forms thereof and for various types of Le$^y$ antigen for use in active immunization has been increasing. However, it has been available only from human cancer tissue or via chemical synthesis as described by Nilsson & Norberg (1987, *Glycoconjugate J.*, 4, 219-223; and 1988, *Carbohydr. Res.*, 183, 71-82), Sato et al. (1987, *Carbohydr. Res.*, 167, 197-210; 1988, *Tetrahedron Lett.*, 29, 5267-5270) and Nicolaou et al. (1990, *J. Am. Chem. Soc.*, 112, 3693-3695).

Preparations from tumor cells provide limited quantities which often contain impurities. On the other hand, pure chemical synthesis involves at least 50 steps, is extremely laborious and results in a poor final yield.

It is toward the objective of providing a low-cost, simplified and greater-yielding synthesis of Le$^x$; dimeric and trimeric Le$^x$ antigens; sialylated forms thereof; and Le$^y$ antigen that the present invention is directed.

SUMMARY OF THE INVENTION

The principal object of the present invention is to provide a low-cost, simplified process for the synthesis of dimeric or trimeric Le$^x$ antigens having improved greater yields.

Another object of the present invention is to provide a low cost, simplified process for the synthesis of sialyl-Le$^x$, sialyl-dimeric Le$^x$, trifucosyl Le$^y$ (VI$^2$FucV$^3$FucIII$^3$FucnLc$_6$) and its higher homologs.

These and other objects of the invention have been achieved by providing a process for preparing difucosyl Y$_2$ antigen (dimeric Le$^x$), the process comprising: (1) preparing a lactonorhexaosylceramide backbone or a lactonorhexaosylsaccharide backbone linked to a carrier molecule; and (2) enzymatically fucosylating the backbone at the III$^3$ and V$^3$ positions through an $\alpha 1 \to 3$ linkage.

The present invention also provides a process for preparing Le$^y$ antigen analogues, the process comprising:

(1) preparing a lactonorhexaosylceramide backbone or a lactonorhexaosysaccharide backbone linked to a carrier molecule;

(2) enzymatically fucosylating the backbone at the terminal $\beta$-Gal through an $\alpha 1 \to 2$ linkage; and (3) enzymatically fucosylating the backbone at one or more positions through an $\alpha 1 \to 3$ linkage, provided that steps (2) and (3) can be conducted simultaneously or in any order.

The present invention also provides a process for preparing an $\alpha 1 \to 2$ and/or $\alpha 1 \to 3$ fucosylated lactonorhexaosylceramide, lactonorhexaosylsaccharide linked to a carrier molecule or higher homologues thereof, said process comprising: (1) preparing a lactonorhexaosylceramide backbone, a lactonorhexaosylsaccharide backbone linked to a carrier molecule or backbones of higher homologues thereof; and (2) enzymatically fucosylating one or more residues of said backbone.

The invention also provides a process for preparing sialylated forms of Le$^x$ and dimeric Le$^x$ using sialylated starting materials such as sialylparagloboside and sialylnorhexaosylceramide, respectively, or using synthetically prepared sialyllactonortetraosyl and sialyllactonorhexaosyl (sialyltetraosyl saccharide and sialylhexaosyl saccharide attached to a carrier molecule (spacer arm), respectively.

BRIEF DESCRIPTION OF DRAWING

FIGS. 1A and 1B outline the synthetic plan for lactonorhexaosyl structure (6) by a (2+2+2) stepwise approach (mode I).

FIGS. 2A and 2B outline the synthetic plan for lactonorhexaosyl structure (6) by a (4+2) block approach (mode II).

FIG. 6 describes the entire procedure for synthesis of lactonorhexaosyl structure (6) by a stepwise approach (mode I) (detailed scheme).

(In FIGS. 1-6, Gal represents galactose, GlcNAc represents N-acetylglucosamine, Glc represents glucose, Ac represents an acetyl group, Bn represents a benzyl group, Bz represents a benzoyl group, Pd-C represents palladium on carbon, Ts represents a tosyl group, $CH_2Cl_2$ is methylene chloride (also known as dicholoromethane), Nphth represents an N-phthalyl group, SMe represents a thiomethyl group, $Bu_3SnSR$ wherein R=alkyl represents thioalkyltributyltin, $Ac_2O$ is acetic anhydride, Py represents pyridine, DMF is N,N-dimethylformamide, MS AW-300 is molecular sieve AW-300, $CH_3CN$ is acetonitrile, $Ce(NH_4)_2(NO_3)_6$ is ceric ammonium nitrate, $(CH_3O)_2C(Me)_2$ is dimethoxypropane, $BnOSnBu_3$ is tributyltin benoxide, DBU is 1,8-diazabicyclo[5.4.0]undec-7-ene, DAST is diethylaminosulfur trifluoride and $(CH_3O)_3CMe$ is trimethylorthoacetate.)

FIG. 7 shows the results of subjecting the monosialoganglioside fraction of bovine red blood cells (RBC) to high performance liquid chromatography (HPLC).

FIG. 8 shows immunostained thin layer chromatographs of enzymatically synthesized dimeric $Le^x$. In FIGS. 8A, 8B and 8C the lanes are as follows: lane 1, lactonoroctylceramide (nLc$_6$), standard from bovine RBC; lane 2, enzyme reaction mixture without nLc$_6$; lane 3, enzyme reaction mixture with nLc$_6$; lane 4, standard dimeric $Le^x$ from human tumor; lane 5, standard "O" upper Folch neutral from human RBC; lane 6, tumor upper Folch neutral.

FIG. 9 is an autoradiogram showing the results of GDP-$^{14}$C-fucose incorporation into nLc$_4$ and nLc$_6$ from bovine and human placenta lactosyl substrates. Lane A, bovine RBC lactoneotetraosylceramide (nLc$_4$) and GDP-$^{14}$C-fucose enzyme reaction mixture; Lane B, human placenta nLc$_4$ and GDP-$^{14}$C-fucose enzyme reaction mixture; Lane C, bovine RBC nLc$_6$ and GDP-$^{14}$C-fucose enzyme reaction mixture; Lane D, numan placenta nLc$_6$ and GDP-$^{14}$C-fucose enzyme reaction mixture.

FIG. 10 shows TLC immunostaining of nLc$_4$ conversion to $Le^x$. In FIGS. 10A, 10B and 10C the lanes are as follows: lane 1, standard "O" upper Folch neutral from human RBC; lane 2, tumor upper Folch neutral; lane 3, tumor $Le^x$ standard; lane 4, enzyme reaction mixture with nLc$_4$ from human placenta; lane 5, enzyme reaction mixture with nLc$_4$ from bovine RBC.

FIG. 11 depicts a plan for synthesizing sialyl-$Le^x$ using sialic acid derivatives (18, 19) and disaccharide substrates (4 and 12).

FIG. 12 depicts a plan for preparing lactosaminyl acceptor (12) which can be used to prepare sialyl-$Le^x$. SEt is thioethyl and IR-120 is Amberlite® ion exchange resin 120.

FIG. 13 depicts a plan for preparing sialyl dimeric $Le^x$ using, for example, the sialylated substrate (8) of FIG. 11 and a tetrasaccharide.

FIG. 14 depicts a plan for preparing tetrasaccharide useful for making sialyl dimeric $Le^x$.

DETAILED DESCRIPTION OF THE INVENTION

Figure 3:
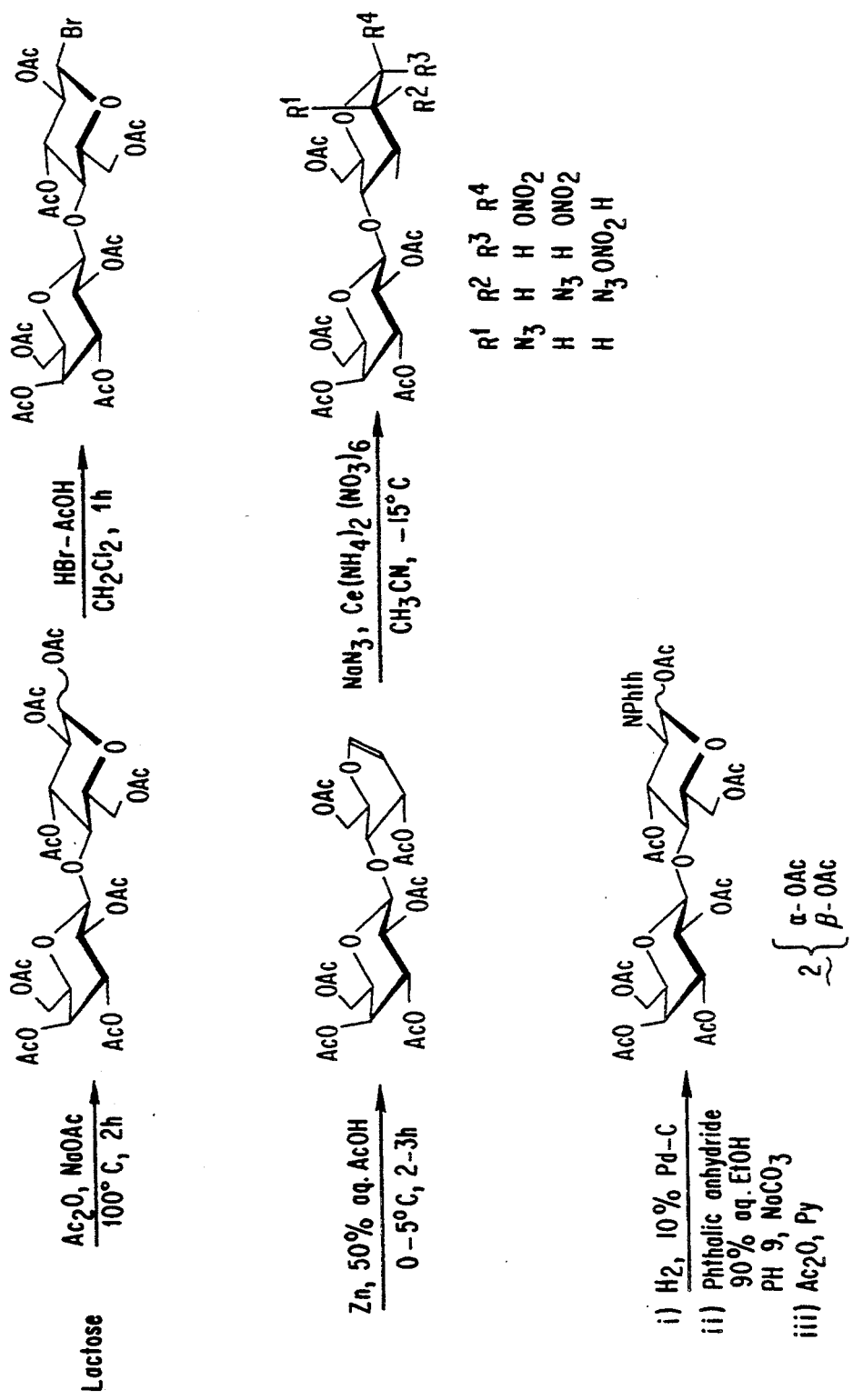
FIG. 3 describes a known synthetic route for O-(2,3,4,6-tetra-O-acetyl-β-D-galactopyranosyl)-(1→4)-1,3,6-tri-O-acetyl-2-deoxy-2-phthalimido-α/β-D-gluocopyranose (2).
Figure 4A:
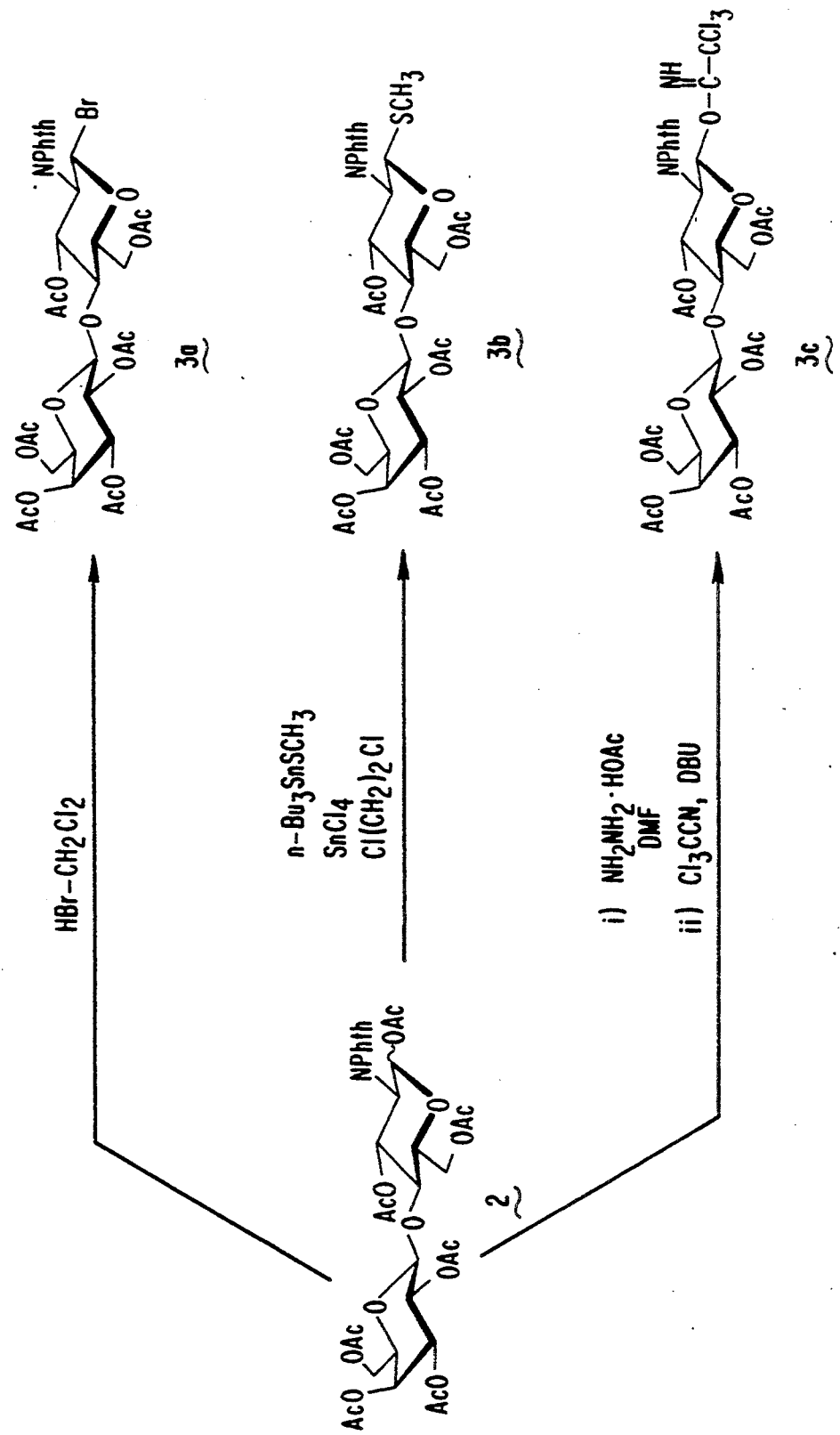
FIGS. 4A and 4B describe the known transformation of (2) into N-phthaloyl-lactosaminyl donors (3a, 3b and 3c).
Figure 4B:
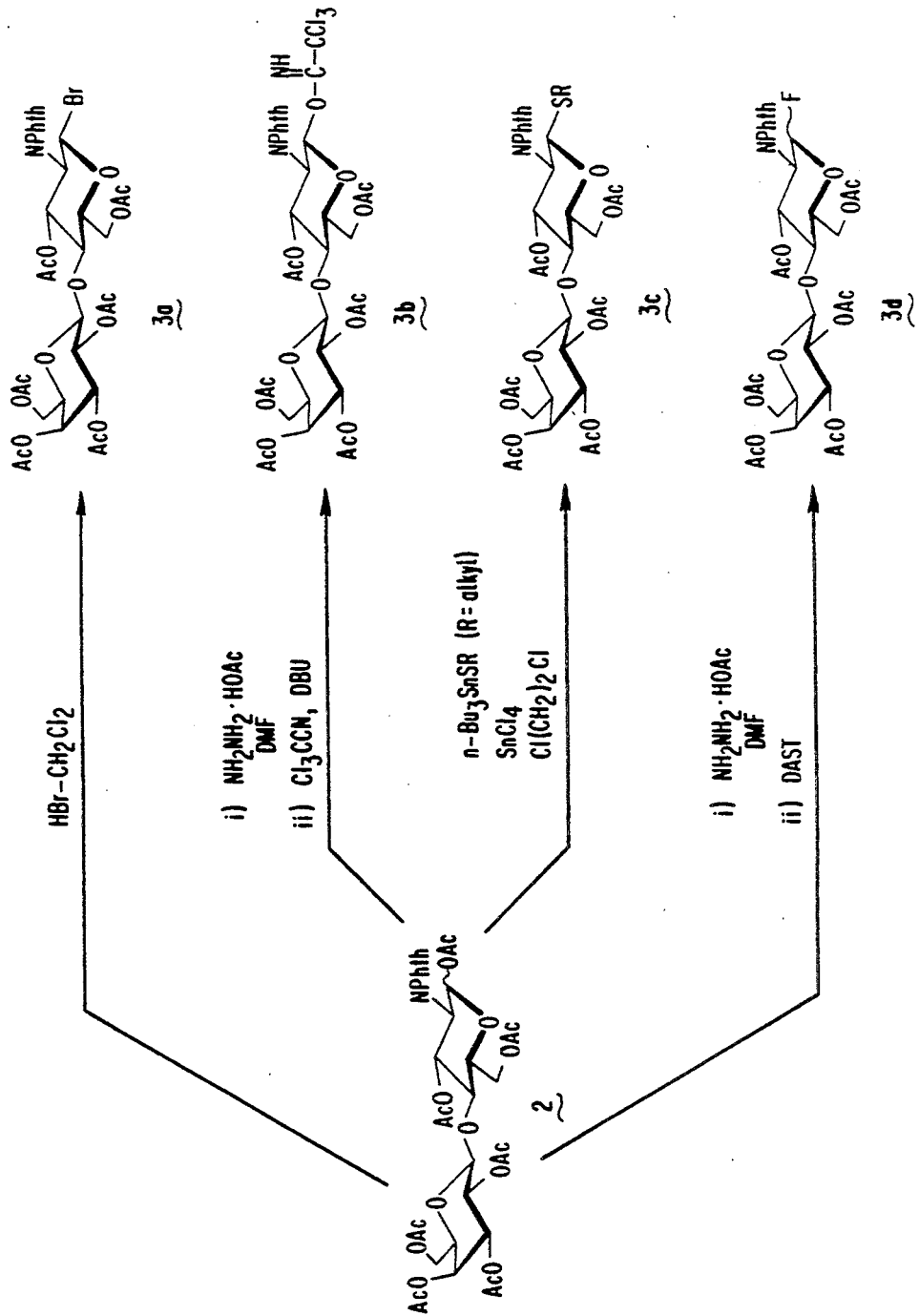
Figure 5:
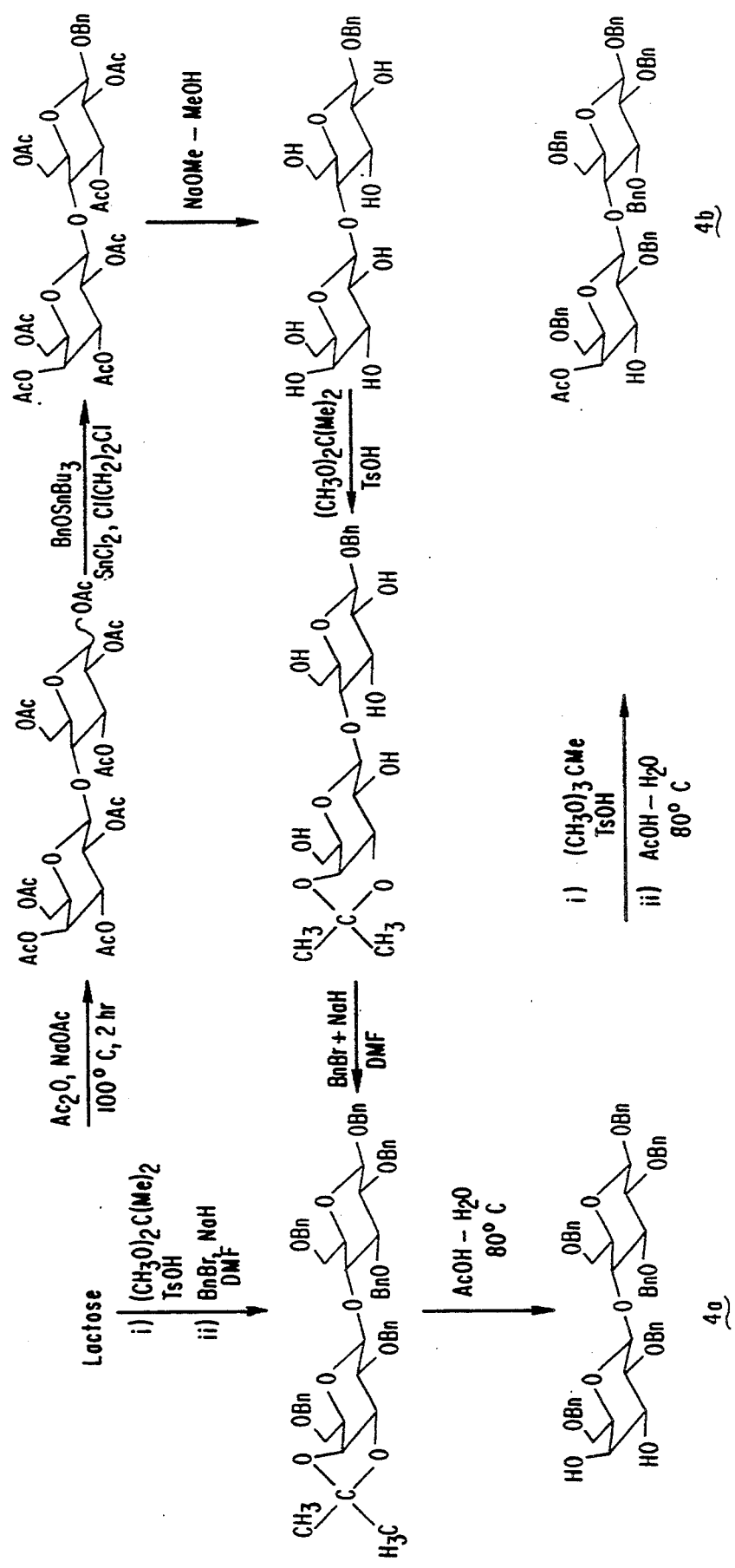
FIG. 5 describes the known synthesis of lactosyl acceptors(4a and 4b).

The present inventors have found the following system highly efficient for synthesis of dimeric $Le^x$ antigen (difucosyl $Y_2$). The backbone structure, i.e., lactonorhexaosyl saccharide or its ceramide conjugate, is synthesized by organic chemical reaction or easily prepared from bovine red blood cells with high yield. Subsequent α1→3 fucosylation at the III$^3$ and V$^3$ positions is carried out by α1→3 fucosyltransferase and GDP-fucose.

The enzyme α1→3 fucosyltransferase is found with high activity in the Colo205 human colon cancer cell line, which has no α1→2 fucosyltransferase activity. Thus, the final product, dimeric $Le^x$ antigen, can be obtained from the backbone structure by a one-step reaction, with 70-80% yield. The overall cost of preparing the antigen in this manner is 1% or less compared to the multi-step chemical synthetic method.

Further, the method can be used to prepare fucosylated analogues of the lactonorhexaosyl structure such as lactonoroctaosyl, lactonordecaosyl or higher homologues (polylactosamines). Examples of compounds, other than the dimeric $Le^x$ antigen, that can be synthesized by the process of the present invention include the $Y_2$ antigen, the $Z_1$ antigen, the $Z_2$ antigen and the $Z_3$ antigen (trimeric $Le^x$). The structures of these compounds along with their short chain analogues are shown in Table I below.

$Le^y$ octasaccharide ceramide, trifucosyl $Le^y$, and $Le^y$ hexasaccharide ceramide are also important human tumor antigens (Abe et al., 1983, J. Biol. Chem. 258, 11793–11797; Nudelman et al., 1986, J. Biol. Chem. 261, 11247–11253; Kaizu et al., 1986, J. Biol. Chem. 261, 11254–11258) and the structures of these compounds are shown in Table II below.

Synthesis of $Le^y$ antigen analogues as in Table II can be made by treating the core carbohydrate chains with α1→2 fucosyltransferase and GDP-fucose followed by α1→3 fucosyltransferase and GDP-fucose, or a combination of these two enzyme reactions. Although a practical experimental example is not given in the application, α1→2 fucosyltransferase can be enriched from colonic cancer cell line MKN74 according to our preliminary experience. Other cell lines that may have higher enzyme activity are also available.

3Galβ1→4Glcβ1→1Cer, or its longer chain analogues, such as lactonoroctaosyl, lactonordecaosyl or higher homologues, can be prepared as glycolipid from a natural source, e.g., from human placenta, bovine red blood cells or rabbit muscle. These tissues and cells contain a large quantity of sialyl 2→6 or 2→3 lactonorhexaosylc-

TABLE I
MONO- AND DIMERIC Le$^x$ ANTIGEN AND RELATED STRUCTURES

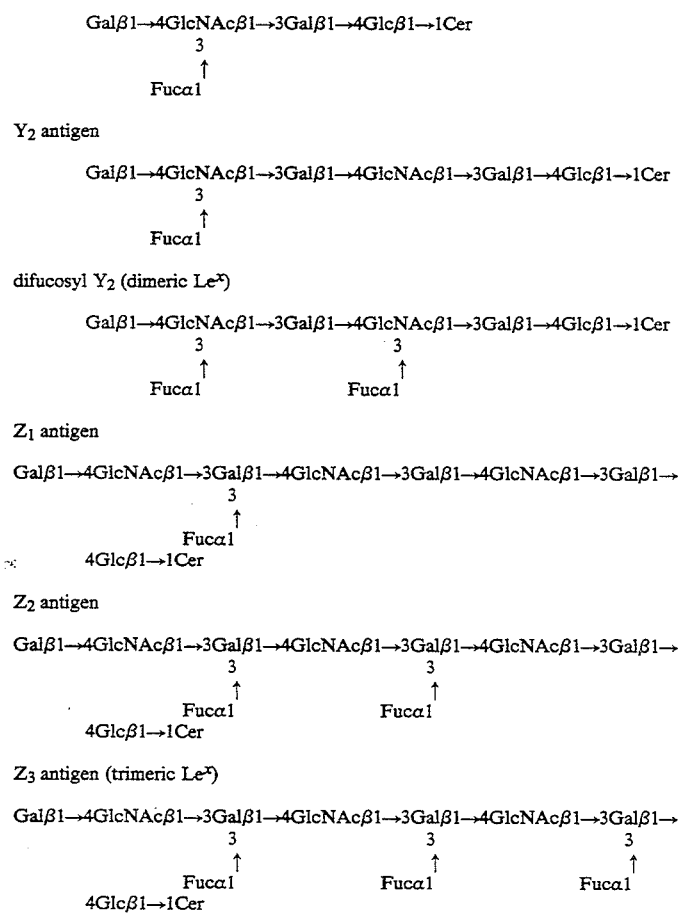

TABLE II
Le$^y$ ANTIGEN AND ANALOGUES

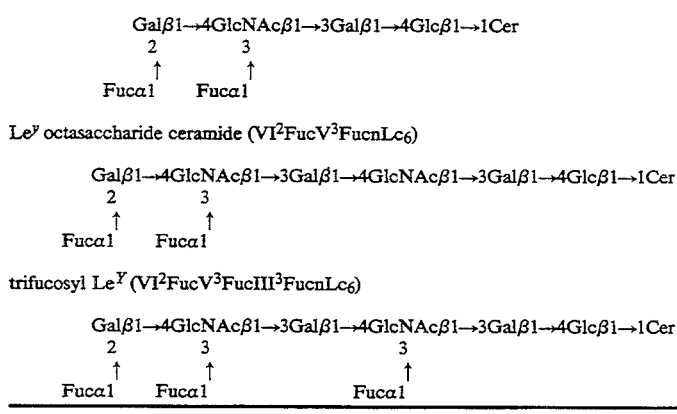

Conditions of synthesis for the method of the present invention are described below.

Lactonorhexaosylceramide, which has the structure, Galβ1→4GlcNAcβ1→3Galβ1→4GlcNAcβ1→ eramide and longer chain analogues thereof, which can be isolated easily by Folch's partition of total lipid extract followed by DEAE-Sepharose chromatography and high performance liquid chromatography in a buffer comprising isopropanol-hexane-water (for detailed procedure see: Hakomori "Chemistry of Glycosphingolipids" In: Handbook of Lipid Research 3: Sphingolipd Biochemistry (Kanfer & Hakomori, eds.), Plenum Publishing, New York, pp. 1-165, 1983). Lactonorhexaosylceramide or its longer chain analogues can be derived from the sialyl counterpart by hydrolysis of the sialic acid with a weak acid (e.g. 1% acetic acid, 80°-90° C. for 1 hr.).

As an alternative to isolation from natural sources, lactonorhexaosylsaccharide or its longer chain analogues linked to carrier molecules such as ceramide or to a protein such as BSA through Lemieux's arm can be synthesized chemically. Such procedures have been described previously (Ogawa, 1987, *Carbohydr. Res.*, 163, 189-208; 167, 197-210; Lemieux et al., 1975, *J. Amer. Chem. Soc.*, 97, 4076-4083). Various synthetic routes starting from lactose and N-phthalyllactosamine are shown in FIGS. 1 to 6.

FIG. 1 shows a synthetic plan for the lactonorhexaosyl backbone 6 by a (2+2+2) stepwise approach. According to this plan the hexasaccharide 6 can be synthesized by the coupling of an N-phthalyl lactosaminyl donor (3a, 3b, 3c or 3d) and a glycotetraosyl acceptor (5), which in turn can be synthesized by the coupling of an N-phthalyl lactosaminyl donor with glycobiosyl acceptor 4. The different lactosaminyl donors 3a (Arnap & Lonngren, 1981, *J. Chem. Soc. Perkin Trans.*, 1, 2070-2074), 3b wherein the X group is 2,2,2-trichloroacetamide (Grundler & Schmidt, 1985, *Carbohydr. Res.*, 135, 203-218; Sadozai et al., 1985, *Carbohydr. Res.*, 157, 101-123), 3c wherein the X group is thioalkyl (Sadozai et al., 1985, supra) and 3d wherein the X group is fluoride (Sadozai et al., manuscript in preparation) can be prepared readily from 2 as described in FIG. 4, which in turn can be synthesized from commercially available lactose in seven steps as described in FIG. 3 (Haworth et al., 1930, *J. Chem. Soc.*, 1930, 2644-2653; Arnap & Lonngren, 1981, *J. Chem. Soc. Perkin Trans.*, 1, 2070-2074). The lactosyl acceptor 4a (R=H, R'=Bn), which has free hydroxyl groups at C-3 and C-4 of the galactose unit (Koike et al., 1987, *Carbohydr. Res.*, 163, 189-208; Paulsen & Paal, 1985, *Carbohydr. Res.*, 137, 39-62) or 4b (R=Ac, R'=Bn), which has a free hydroxyl group only at C-3 of the galactose unit (Yoshino et al., 1988, *Glycoconjugate J.*, 5, 377-384) can also be prepared from lactose 1 by known procedures as described for example in FIG. 5.

Due to the higher reactivity of the 3'-OH groups, the glycosylation of 3b with 4a preferentially gives the tetrasaccharide 7a with its (1→4) analogue 8a as a minor product (FIG. 6)(Paulsen & Michael, 1987, *Carbohydr. Res.*, 169, 105-125; Ito & Ogawa, 1986, *Agric. Biol. Chem.*, 50, 3231-3233). Alternatively, the glycosylation of 4b with 3b gives only one tetrasaccharide 7b in much better yield. Both of the tetrasaccharides 7a and 7b can be converted either to 5a by the reaction steps: (i) sodium methoxide-methanol (NaOMe-MeOH); ii) dimethoxypropane and p-toluenesulfonic acid (p-TsOH); iii) BnBr—NaH-DMF; and iv) AcOH—H$_2$O, 80° C.; or to 5b by the reaction steps: (i) NaOMe-MeOH; ii) trimethylorthoacetate/p-TsOH/benzene; iii) BnBr—NaH-DMF; and iv) AcOH—H$_2$O, 80° C. Glycosylation of the glycotetraosyl acceptor 5a with 3b then gives the desired protected hexasaccharide 9a and its (1→4) analogue 10. On the other hand, the glycosylation of 5b with 4b is expected to give only one product 9b in better yield. Each of the protected hexasaccharides 9a or 9b can be converted to deblocked lactonorhexaosyl 6 by the following reactions [(i) NaOMe-MeOH, ii) NH$_2$NH$_2$—H$_2$O-EtOH, reflux, iii) Ac$_2$O-MeOH, iv) 10% Pd—C, H$_2$].

In FIG. 2, an alternative synthetic route (4+2 block approach, mode II) to 6 is shown, which differs from the (2+2+2) stepwise approach mode I (FIG. 1) in the sense that two N-phthalyl lactosaminyl disaccharides can be coupled to get a tetrasaccharide and then that tetrasaccharide can be coupled to the lactosyl acceptor to give the hexasaccharide. According to this possible plan, the thioglycoside 3c can be transformed into a lactosaminyl acceptor 11 (FIG. 14) and then glycosylated with another lactosaminyl donor 3 (FIG. 4) to give a tetrasaccharide 12. The tetrasaccharide thus obtained can be used as such as a donor by activating the anomeric thioalkyl group by the use of an appropriate catalyst and coupled to known lactosyl acceptor 4 to give the protected hexasaccharide 13. The protected hexasaccharide can be transformed into the free 6 in the same manner as described for 9 (FIG. 6).

Subsequently, the lactonorhexaosylceramide or analogues thereof derived from natural sources or chemically synthesized lactonorhexaosylsaccharide or analogues thereof can be converted quantitatively to their α1→3 fucosyl derivatives as shown below:

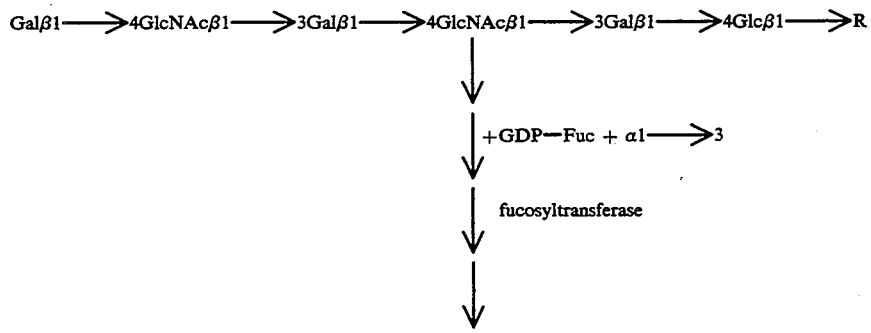

-continued

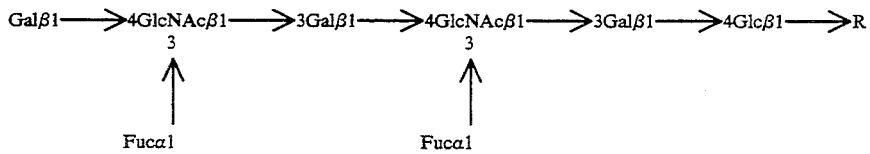

where R represents ceramide or a carrier molecule.

Any source of $\alpha1\to3$ fucosyltransferase can be used. Some of the preparations, depending on the source, may contain $\alpha1\to4$ fucosyltransferase or a non-specific enzyme that has both $\alpha1\to3$ and $\alpha1\to4$ transferase activities. However, lactonorhexaosyl and longer lactonorhexaosyl structures have no free OH group at the C4 position of GlcNAc, and therefore, the presence of $\alpha1\to4$ fucosyltransferase activity does not change the quality of the product, i.e., the product has exclusively $\alpha1\to3$ fucosyl substitution.

Sources other than Colo205 include human colonic mucosa and human colonic adenocarcinoma cell lines.

Example II describes the reaction using the enzyme from the human colonic adenocarcinoma Colo205 cell line. This cell line contains $\alpha1\to3$ and $\alpha1\to4$ fucosyltransferase, but does not contain $\alpha1\to2$ fucosyltransferase. Any of the other cell lines or tissues can be used if appropriate enzymatic activities are present.

In an analogous manner, structures related to the Le$^x$ antigen can also be prepared.

For example, the Y$_2$ antigen can be prepared by $\alpha1\to3$ fucosylation at the V$^3$ position of the lactonorhexaosyl backbone, and the Z$_1$ antigen, Z$_2$ antigen and Z$_3$ antigen can be prepared by $\alpha1\to3$ fucosylation at the VII$^3$ positions only, the V$^3$ and VII$^3$ positions and the III$^3$, V$^3$ and VII$^3$ positions, respectively, of the lactonoroctaosyl backbone.

Further enzymatic synthesis could also include $\alpha1\to3$ fucosylation at the V$^3$ position and $\alpha1\to2$ fucosylation at the terminal galactose residue of lactonorhexaosyl backbone to give the Le$^Y$ structure and this could be further converted to trifucosyl Le$^Y$ by $\alpha1\to3$ fucosylation at the III$^3$ position.

Enzymatic synthesis could also include $\alpha1\to4$ fucosylation etc., so long as a useful structure is produced.

The $\alpha1\to3$ fucotransferase and $\alpha1\to4$ fucotransferase enzyme preparations can be made from known sources as described above, by known methods such as described in Example II. (Holmes et al., 1985, J. Biol. Chem., 260, 7619–7627).

Although actual examples of synthesis of Le$^y$ antigen are not included in this application, Le$^y$ antigens can be synthesized by addition of fucose at the terminal Gal residue with $\alpha1\to2$ fucosyltransferase and GDP-fucose followed by the action of $\alpha1\to3$ fucosyltransferase and GDP-fucose by analogous procedures to those followed for synthesis of dimeric Le$^x$ antigen.

The enzyme $\alpha1\to2$ fucotransferase capable of fucosylating a terminal galactose residue has been found in the MKN74 colonic cancer cell line although its activity is relatively weak and concentration of the enzyme is necessary. Since $\alpha1\to2$ fucosyl transferase is widely found in various cells, better sources of $\alpha1\to2$ fucosyl transferase are highly plausible. Thus a possibility for the following synthesis of Le$^y$ or Le$^y$ octasaccharide ceramide is envisioned to be within the scope of the invention.

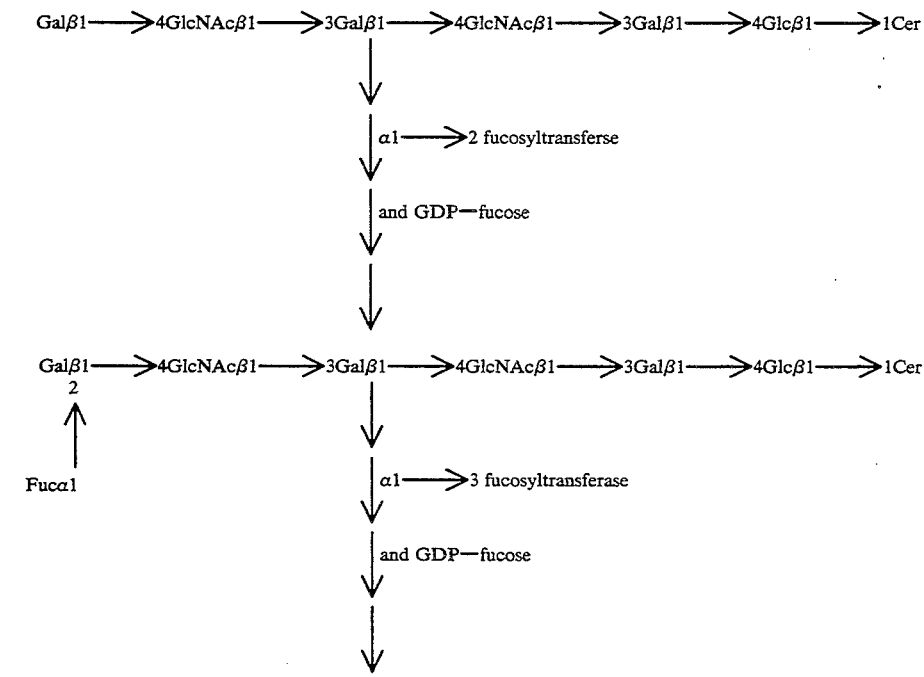

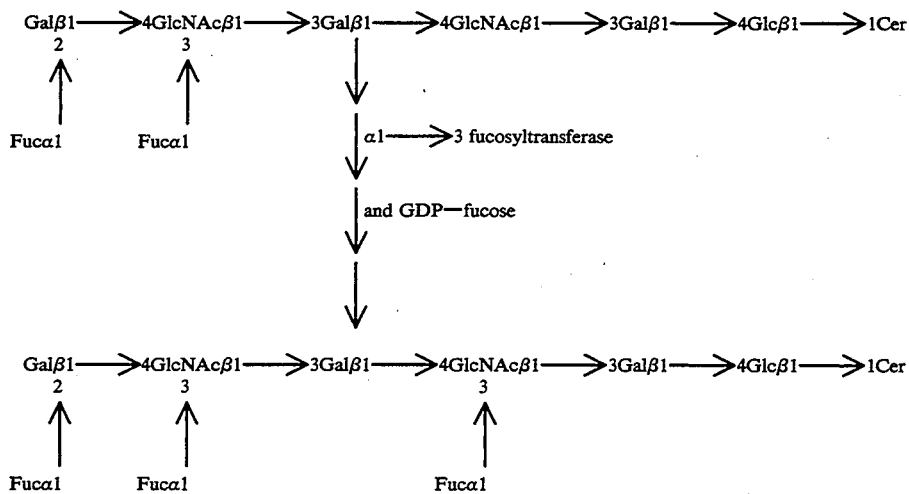

(trifucosyl Le^y antigen, an important tissue-associated antigen)

GDP-fucose can be synthesized from fucose β1-phosphate by known methods (Nunez et al., 1981, *Can. J. Chem.*, 59, 2086–2095; Michelson, 1964, *Biochim. Biophys. Acta*, 91, 1–13).

Sialylated forms of dimeric Le$^x$ and derivatives thereof can be synthesized essentially in the same fashion as described above except that sialylated forms of the initial glycolipid substrates are used.

Figure 7A:
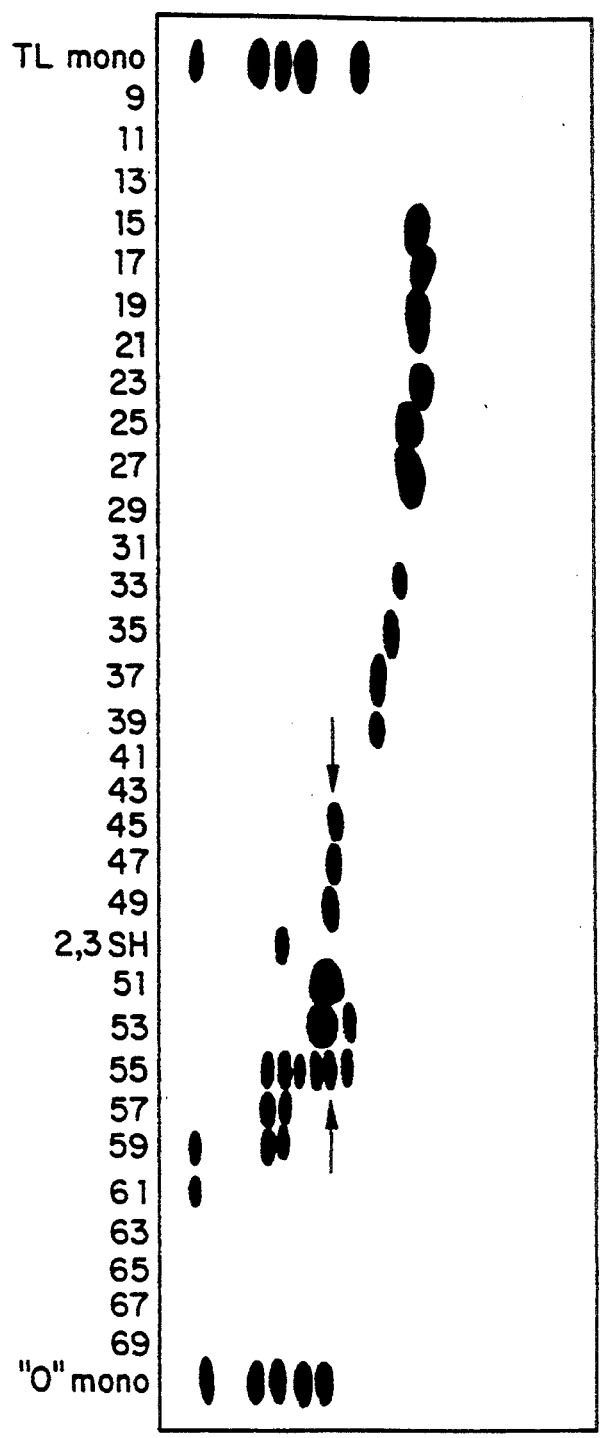
FIG. 7A shows the elution pattern of the monosialyl gangliosides through an Iatrobead column. The arrow indicates sialylnorhexosyl ceramide.

Enzymatic synthesis of sialyl-Le$^x$ and sialyl-dimeric Le$^x$ is performed as described in Example II, however, the glycolipid substrates used are sialylparagloboside (IV$^3$NeuAcnLc$_4$) and sialynorhexaosylceramide (VI$^3$-NeuAcnLc$_6$), respectively. Both substrates are obtained from bovine red blood cells as described in Example I, with the exception that step 3, "Hydrolysis with Acetic Acid", is omitted. Sialylparagloboside can be obtained in fractions 37–39 as shown in FIG. 7A. All procedures are performed as described for the bio-organic synthesis of dimeric Le$^x$ and its analogues with the exception of the aforementioned substrate modifications.

Alternatively, as shown in FIG. 11, sialyl Le$^x$ 14 can be synthesized by enzymatic fucosylation of sialosyl lactoneotetraose 15, which can be synthesized chemically by the coupling of a sialic acid containing trisaccharide donor 16 with a disaccharide acceptor 17. To achieve this chemical synthesis, compound 18 as a synthetic equivalent of sialolactosaminyl donor 16 and compound 4 (FIG. 1) as a synthetic equivalent of lactosyl acceptor 17 could be used. The glycotriosyl donor 18 can be obtained by glycosylation of lactosaminyl acceptor 12 (FIG. 11) with sialosyl donor 19 (Kuhn et al., 1966, *Chem. Ber.*, 99:611). The lactosaminyl acceptor 12 is synthesized from known compound 2 (FIG. 3) (Arnap & Lonngren 1981, *J. Chem. Soc. Perkin Trans.*, 1:2070–2074) according to the reaction sequence described in FIG. 12.

Sialyl Le$^x$ linked to a spacer arm (or linker arm) can also be synthesized by the same strategy using a lactosyl acceptor 4c (R=(CH$_2$)$_n$COOCH$_3$) having a spacer arm already attached to the lactose.

Sialyl dimeric Le$^x$ 20 in FIG. 13 can be synthesized via enzymatic fucosylation of, for example, heptasaccharide 21 which can be synthesized chemically. To synthesize 21, sialolactosaminyl donor 18 (FIG. 11) is coupled to the tetrasaccharide acceptor 5a, 5b or 5c which can be synthesized as depicted in FIG. 14. The reaction scheme to make the tetrasaccharide acceptor is similar to the scheme presented in FIG. 6.

The synthesis of large quantities (gram amounts) of sialyl-dimeric Le$^x$ oligosaccharides also may be accomplished conveniently using the hexasaccharide, Galβ1→4GlcNAcβ1→3Galβ1→4GlcNAcβ1→3Galβ1→4Glc (6), which is synthesized as shown in FIG. 1 or as in FIG. 2 or FIG. 6. Once the oligosaccharide is obtained, the terminal sialyl residue may be attached according to the reaction shown on the next page:

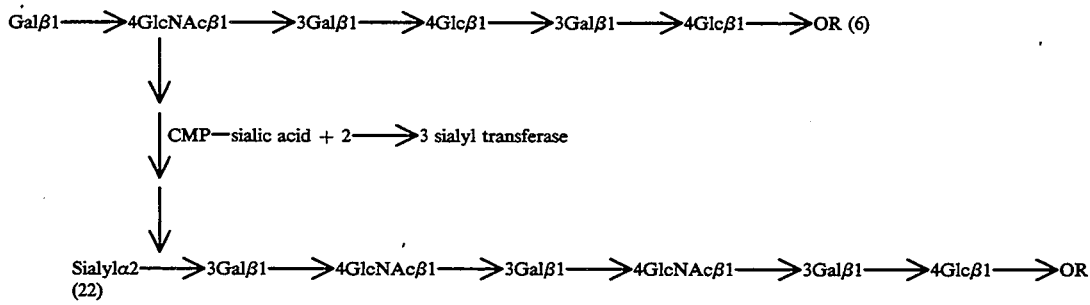

compound 4 (FIG. 1) as a synthetic equivalent of lactosyl acceptor 17 could be used. The glycotriosyl donor 18 can be obtained by glycosylation of lactosaminyl Addition of fucose to the GlcNAc residues of sialylated oligosaccharide (22) is quantitative according to the reaction:

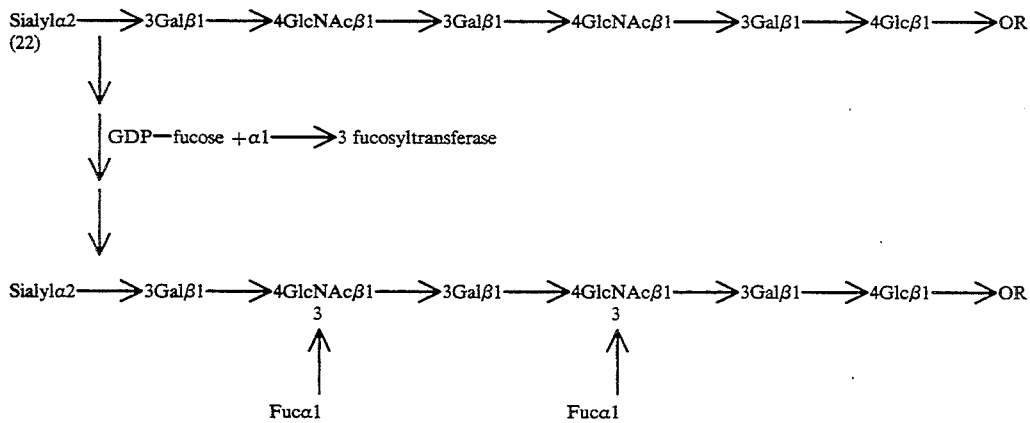

Similarly, Sialyl Le$^x$ may be synthesized according to the two enzymatic reactions:

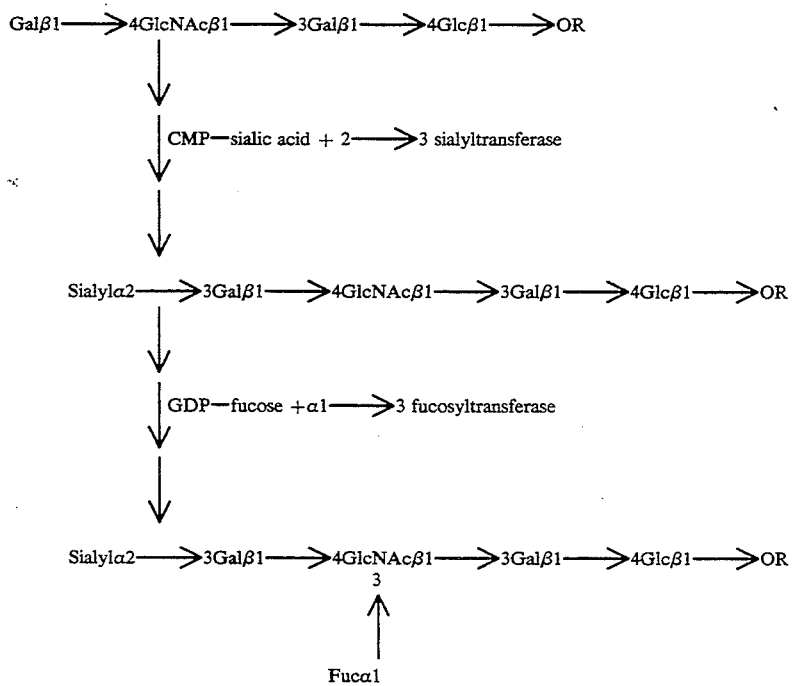

The present invention will now be described by reference to specific examples, but the examples are not to be construed as limiting the invention.

Unless otherwise specified, all percents, ratios, parts etc. are by weight.

EXAMPLE I

PREPARATION OF CORE LACTONORHEXAOSYL STRUCTURE

Five gallons of fresh bovine red blood cells were obtained from a local slaughterhouse in the form of unlysed, citrated whole blood. The five gallons were diluted to fifteen gallons by adding deionized H$_2$O at 4° C. and acetic acid was added to a final concentration of 0.1%. After stirring, the red blood cells were allowed to lyse overnight at 4° C. The following morning, the lysed blood was centrifuged in a preparative rotor (Beckman JCF-Z), and the pellet was washed with H$_2$O. From five gallons whole blood, a 1.8 liter pellet of pinkish stroma was obtained.

1. Homogenization

The stroma pellet was homogenized in three liters of ethanol for three minutes and then brought to slow boil in an 80° C. water bath for five minutes. The hot ethanol extract was filtered over a Büchner funnel and the residue rehomogenized in the same manner an additional two times. The three filtrates were pooled and evaporated to dryness by rotovap. The organic residue was transferred to a gallon jug in three liters of chloroform-methanol (2:1, v:v) and 500 ml of H$_2$O were added. The solution was shakened ten times to form Folch's partition. After the upper phase cleared, it was suctioned off, and the volume was replaced with chloroform-methanol-water (1:10:10, v:v:v; 0.1% KCl). After the phases separated, the second upper phase was drawn off. The two pooled upper phases were evaporated to dryness by rotovap and dialyzed in a Spectrapor membrane (S.P.) 3 (M.W cutoff=3500) against water for two days.

A 300 ml bed volume of DEAE Sephadex (Sigma) was used in a column 5 cm×25 cm. The Sephadex was pre-equilibrated with chloroform-methanol-water (30:60:8, v:v:v; 0.8M sodium acetate) overnight and washed in chloroform-methanol-water (30:60:8, v:v:v). The dialyzed upper phase was evaporated to dryness by rotovap and brought up in 500 ml chloroform-methanol-water (30:60:8, v:v:v, Sol A). This was applied to DEAE and washed with 2 liters Sol A.

The column was washed with 500 ml methanol, and the monosialoganglioside fraction (containing sialylnorhexaosylceramide) was eluted in 0.04M ammonium acetate (1.5 liters). The monosialyl fraction was evaporated to dryness, dialyzed for three days against water, evaporated by rotovap and transferred to a 15 ml screw cap tube.

2. Separation of Monosialyl Fraction by HPLC

A 50 cm×1 cm column of Iatrobeads (10 μm; Iatron 6RS-8010) was pre-equilibrated as follows. A starting composition of 2-propanol-hexane-water (55:25:20, v:v:v) at 2.0 ml/min was applied and a linear gradient to a final composition of 55:40:5 (v:v:v) was applied over 120 min. The sample was applied in two injections of 2 ml in chloroform-methanol-water (2:1:0.1, v:v:v) at a starting composition of 55:40:5 (v:v:v) at 0.5 ml/min. The gradient was changed to 55:25:20 (v:v:v) after 400 min and remained at this composition for a final 100 min (t=500 min). Fractions were collected in 100 tubes, 2.5 ml/tube. Fractions were chromatographed in chloroform-methanol-water (50:40:10, v:v:v) containing 0.05% $CaCl_2$ (Merck HPTLC plates) and detected by 10% $H_2SO_4$-0.5% orcinol. The fractions containing sialyllactonorhexaosylceramide (fractions 55-58) were pooled and further purified by chromatography on a long Iatrobead 6RS-8010 column (0.5 cm×100 cm) pre-equilibrated with isopropanol-hexane-water (55:40:5, v:v:v). The column was eluted by gradient elution using isopropanol-hexane-water (55:40:3 to 55:25:20, v:v:v) over 300 minutes, then eluted with the same solvent for 400 minutes. Essentially pure sialyllactonorhexaosylceramide was obtained.

The results are shown in FIG. 7.

In FIG. 7, TLC was performed by conventional methods. FIG. 7A is a thin layer chromatogram showing the elution pattern of monosialyl gangliosides through the Iatrobead column. The arrow indicates sialylnorhexaosyl ceramide.

Figure 7B:
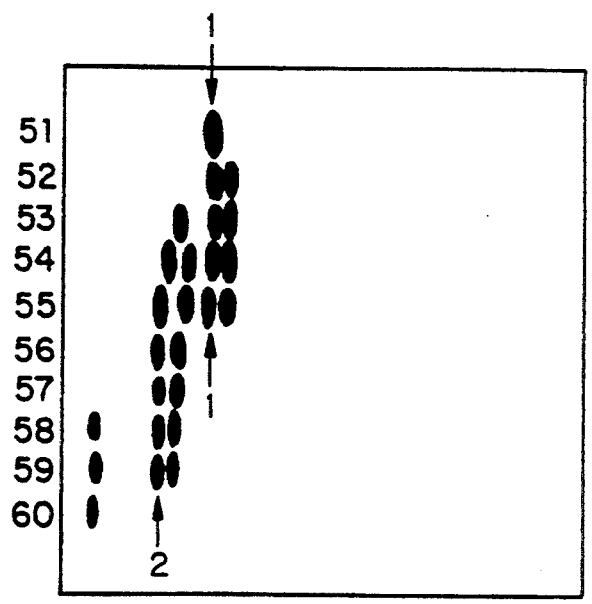
FIG. 7B shows the thin layer chromatograph of fractions 51 to 59. Arrow 1 indicates sialyl lactonoroctaosylceramide and arrow 2 indicates sialyl lactoisooctaosylceramide.

FIG. 7B shows a thin layer chromatographic pattern of fractions 51-59. Arrow 1 indicates sialyl lactonoroctaosylceramide and arrow 2 indicates sialyl lactoisoooctaosylceramide. The fractions noted are the major sources for the preparation of lactonorhexaosylceramide (Gal$\beta$1→4GlcNAcB1→3Gal$\beta$1→4GlcNAc$\beta$1→3Gal$\beta$1→4Glc$\beta$1→1Cer) and lactoisooctaosyl-ceramide (I antigen), respectively.

Figure 7C:
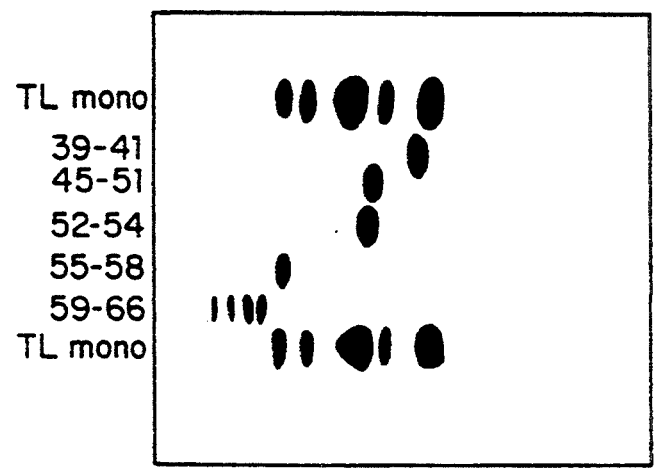
FIG. 7C shows the thin layer chromatograph of several pooled fractions.
Figure 7D:
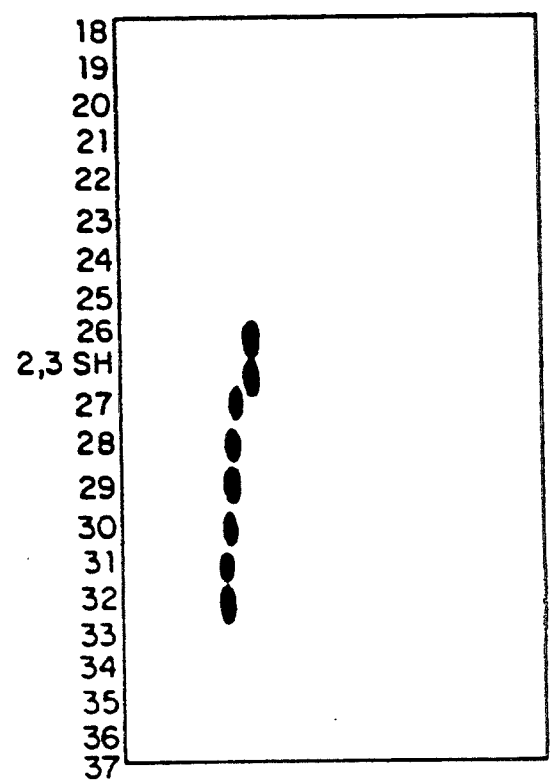
FIG. 7D shows the separation pattern after the pooled fractions 55–58 in FIG. 7C were subjected to a second HPLC.

FIG. 7C shows the thin layer chromatographic pattern of several pooled fractions. The pooled fraction (55-58) in FIG. 7C was subjected to a second HPLC run and the separation pattern is shown in FIG. 7D.

3. Hydrolysis with Acetic Acid

Two milligrams of sialyllactonorhexaosylceramide was evaporated to dryness in an 8 ml screw cap tube and 1 ml of 1.0% acetic acid added. The tube was placed in a 100° C. heat block for 1 hr. After hydrolysis, the sample was evaporated to dryness by adding 2 ml ethanol and drying under an $N_2$ stream. The dried glycolipid was dissolved in 2 ml of water and applied to a Sep-Pak C-18 reverse phase column, washed intensively with water and eluted with methanol. The eluate was evaporated. The reaction was quantitative.

EXAMPLE II

ENZYMATIC α1→3 FUCOSYLATION

Fifty grams of solid tumors in nude mice (40-50 tumors combined) were homogenized on ice in 100 ml of 50 mM Tris buffer pH 7.4, 1% Triton X-100, 2 mM $MnCl_2$, and 25% glycerol and particulate matter was separated. The supernatant was used as the enzyme source (Preparation I).

GDP-fucose, the sugar donor, is available commercially or can be produced from fucose β1-phosphate (Nunez et al., 1981, Can. J. Chem., 59, 2086-2095; Michelson, 1964, Biochem. Biophys. Acta, 91, 1-13).

The enzymatic reaction was carried out in various scales. The following description indicates one example. Ten milligrams of lactonorhexaosylceramide (nLc$_6$) or lactonorhexaosyl oligosaccharide was mixed with 2 mg of sodium taurocholate in a 100 ml round bottom flask, codissolved in a suitable solvent, thoroughly mixed and evaporated to dryness. The dried residue was dissolved in 1 ml of water, 50 μl of 0.4M $MnCl_2$ and 500 μl of 1.0M Tris buffer pH 7.4, sonicated well and mixed with 500 μl of aqueous solution containing 50 mg CDP-choline (Sigma) and 10 mg GDP-fucose.

The total mixture was then added to 10 ml of the enzyme "Preparation I". The reaction then proceeded at 37° C. with shaking. After 18 hr, 100 mg CDP-choline and 20 mg GDP fucose in 1 ml $H_2O$ were added and the reaction was left another 24 hrs.

The entire reaction mixture, when starting from lactonorhexaosylceramide, was then applied to a C18 HPLC column and washed extensively with water to eliminate all water-soluble components in the reaction mixture. Glycolipids were eluted from the column with methanol followed by chloroform-methanol (2:1, v:v), then further purified on HPLC with an isopropanol-hexane-water system using known methods.

The reaction mixture, when starting from lactonorhexaosyl oligosaccharide linked to a carrier peptide or protein, was placed on an affinity column containing an antibody which reacts with dimeric Le$^x$ (an example of such an antibody is SH2 available from The Biomembrane Institute, Seattle, Wash.). The compound was diluted with 1-2M NaCl. Under these conditions, about 60-70% of the norhexaosyl structure was converted to dimeric Le$^x$, based on orcinol detection of resultant glycolipid product. A TLC plate was chromatographed and detected by 0.5% oricinol in 10% $H_2SO_4$, heated at 150° C. for 3 minutes. Percentage conversion was based upon densitometer readings giving area units for each band. About 10% was not converted and about 20-30% was converted to the monofucosyl derivative.

Thus, the method of fucosylation can be summarized as presented in flow diagram on the next page.

Summary of Enzymatic α1→3 Fucosylation

1. Enzyme Sources:
   a) Human Colonic Mucosa
   b) Human Colonic Adenocarcinoma Cell Lines
      Colo205, human intestine, etc.
      Crude homogenate
      Golgi-enriched fraction
      Detergent soluble fraction
      Semi-purified (ion exchange, GDP hexanolamine, etc.)

-continued

Summary of Enzymatic α1→3 Fucosylation 50 gm solid tumors grown in nude mice (40-50 tumors).
Place in 100 ml of 50 mM Tris pH 7.4, 1% Triton X-100,
2 mM MnCl$_2$ and 25% glycerol and homogenize on ice.
↓
Spin 100,000 g
Supernatant is enzyme prep I.

2. Nucleotide sugar

GDP-fucose can be obtained commercially or produced from fucose β1-phosphate as described above.

3. Reaction Mixture 10 mg of nLc$_6$ from human placenta (100% pure) was dried with 2 mg taurocholate 100 ml round bottom by rotovap. To this was added:

500 μl of 0.4 m MnCl$_2$ (200 μ moles)
500 μl of 1.0 m Tris pH 7.4
1.0 ml H$_2$O sonicated and mixed
↓
Add 50 mg CDP-choline in 500 μl H$_2$O
10 mg GDP-fucose (Biocarb) in 500 μl H$_2$O
↓
Plus 10 mls of Colo205 tumor enzyme prep I.

Reaction was allowed to proceed overnight at 37° C. with shaking. After 18 hours, CDP-choline and GDP-fucose were added (Doubling amount added in each case) and reaction left another 24 hours. At this point about 60–70% of nLc$_6$ had been converted to dimeric Le$^x$. About 10% was unconverted and about 20–30% was converted to monofucose glycolipid.

Various assays were then performed to characterize the reaction products.

The results are shown in FIGS. 8, 9 and 10.

In FIGS. 8, 9 and 10, TLC was carried out according to known methods, as was orcinal staining and immunostaining with antibodies that bind to Le$^x$ and to dimeric Le$^x$ (such as SH1 which is available from The Biomembrane Institute, Seattle, Wash.) and that bind to dimeric Le$^x$ only (such as SH2 which is available from The Biomembrane Institute, Seattle, Wash.).

To obtain the autoradiograms of FIG. 9, reaction mixtures were spotted at 2000 cpm/lane and the film was esposed for 18 hours.

Figure 8A:
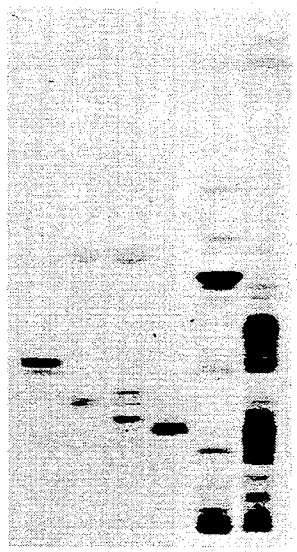
FIG. 8A shows the pattern after staining with orcinol and $H_2SO_4$, which detects carbohydrate.
Figure 8B:
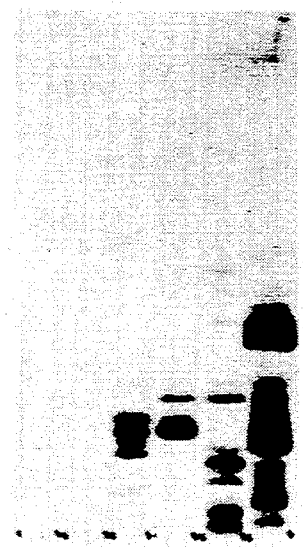
FIG. 8B shows the pattern after staining with monoclonal antibody SH1, which detects long and short chain $Le^x$ glycolipid.
Figure 8C:
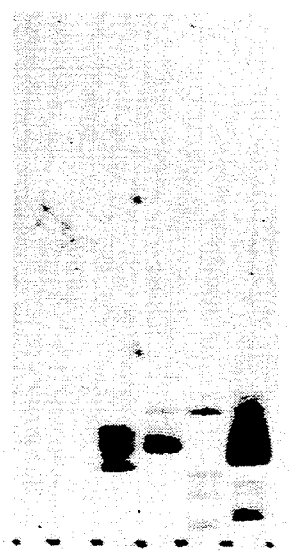
FIG. 8C shows the pattern after staining with monoclonal antibody SH2, which detects only long chain $Le^x$ (dimeric $Le^x$).

FIG. 8 shows thin layer chromatographs immunostained for enzymatically synthesized dimeric Le$^x$ using primary antibodies as shown, secondary rabbit antimouse antibodies and finally iodinated $^{125}$I-protein A according to known methods. FIG. 8A shows the pattern after staining with 0.5% orcinol, 10% H$_2$SO$_4$ by known methods. Orcinol staining detects carbohydrate. FIG. 8B shows the TLC pattern after immunostaining with monoclonal antibody SH1, detecting long and short chain Le$^x$ glycolipid. FIG. 8C shows the TLC pattern after immunostaining with SH2 which detects only long chain Le$^x$ (dimeric Le$^x$). Lane 1, nLc$_6$ standard from bovine RBC; lane 2, enzyme reaction mixture without nLc$_6$ (the fast migrating ban is sodium deoxycholate, the lower band is derived from impurity in the enzyme preparation); lane 3, enzyme reaction mixture with nLc$_6$; lane 4, standard dimeric Le$^x$ from human tumor; lane 5, standard "O" upper Folch neutral from human RBC; lane 6, tumor upper Folch neutral. Note conversion of nLc$_6$ to dimeric Le$^x$ in lane 3 as seen by orcinol detection (FIG. 8A) as well as immunostaining with anti-Le$^x$ (FIGS. 8B and 8C).

FIG. 9 is an audioradiogram showing the results of the incorporation of $^{14}$C-fucose into nLc$_4$ and nLc$_6$ from bovine and human placenta lactosyl substrates. Lane A depicts the bovine RBC nLc$_4$ and $^{14}$C-fucose enzyme reaction mixture; Lane B, the human placenta nLc$_4$ and $^{14}$C-fucose enzyme reaction mixture; Lane C, the bovine RBC nLc$_6$ and $^{14}$C-fucose enzyme reaction mixture; and Lane D, the human placenta nLc$_6$ and $^{14}$C-fucose enzyme reaction mixture. The appearance of two doublets was noted in conversion of nLc$_6$ denoting the addition of one and two fucose residues, respectively. The intermediate product, with only one fucose added, is not reactive with SH1 (FIGS 10B and 10C, lane 3) and therefore, fucose is added internally and not at the terminal GlcNac (i.e., Le$^x$ epitope).

Figure 10A:
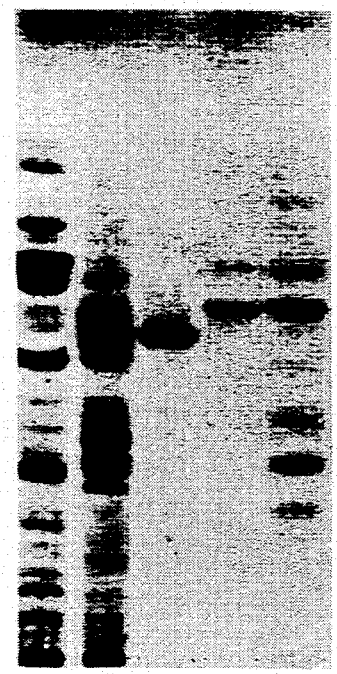
FIG. 10A shows the pattern after staining with orcinol-$H_2SO_4$.
Figure 10B:
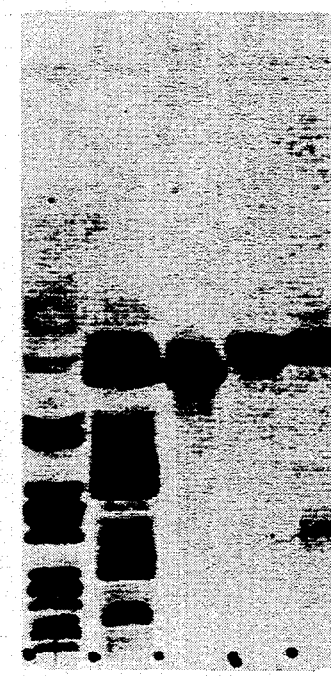
FIG. 10B shows the pattern after staining with anti-$Le^x$ antibody SH1.
Figure 10C:
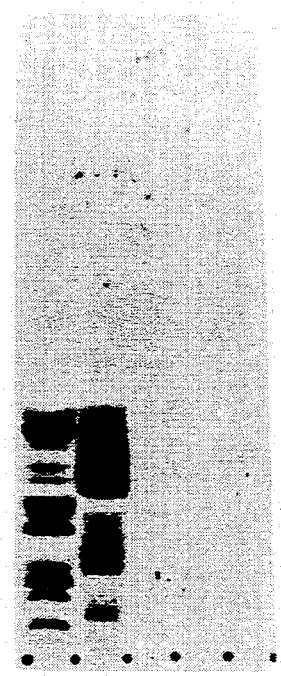
FIG. 10C shows the pattern after staining with anti-dimeric $Le^x$ antibody SH2.

FIG. 10 shows TLC immunostaining of nLc$_4$ conversion of Le$^x$. FIG. 10A shows detection with orcinol-H$_2$SO$_4$ as in FIG. 8A. FIG. 10B shows the immunostaining pattern with anti-Le$^x$ antibody, SH1. FIG. 10C shows immunostaining with anti-dimeric Le$^x$ antibody, SH2. Lane 1, standard "O" upper Folch neutral; lane 2, tumor upper Folch neutral; lane 3, tumor Le$^x$ standard; lane 4, enzyme reaction mixture with nLc$_4$ from human placenta; and lane 5, enzyme reaction mixture with nLc$_4$ from bovine RBC. FIG. 10B, lanes 4 and 5 show SH1-positive reaction demonstrating production of the Le$^x$ epitope. SH2 does not stain short-chain Le$^x$.

As already discussed above, many of the fucosylated structures produced according to the present invention are useful as active vaccines for tumors. The skilled artisan can readily determine which structures are useful for which tumors. Further suitable pharmaceutically acceptable carriers, diluents or excipients for the vaccine, suitable methods of administration and doses can be determined readily by the skilled artisan.

Dimeric Le$^x$ has been shown to be useful to suppress the appearance of inflammatory granulocytes in the bone marrow of RA-affected joints.

Many of the structures will be useful for producing monoclonal antibodies with specific binding for that substance. Such monoclonal antibodies can be used for passive immunization against tumors and for in vitro and in vivo methods of detecting tumors. Such methods are readily known to and conducted by the skilled artisan.

EXAMPLE III

SYNTHESIS OF Le$^y$ ANTIGEN

A series of Le$^y$ antigens can be prepared by a similar enzymatic fucosylation as that applied for synthesis of dimeric Le$^x$ described above. Lactonorhexaosylceramide or lactonorhexaosyl saccharides linked to carrier molecules or their higher analogues are the starting materials. The material is dissolved in Tris buffer in the presence of bivalent cation and appropriate detergent such as taurocholate, as described above. To the solution is added GDP-fucose, CDP-choline, and α1→2 fucosyltransferase, which is isolated from human gastric cancer cell line MKN74 or the same enzyme isolated from any other source. The reaction can be similarly processed as described above and subsequently α1→2 fucosylated derivatives will be isolated, which can be monitored by positive reaction with monoclonal antibody BE2 (Young et al., 1981, *J. Biol. Chem.*, 256, 10967–10972). The H-active compound as an intermediate can be further processed for α1→3 fucosylation by α1→3 fucosyltransferase of Colo205 and GDP-fucose under the same conditions as described above for dimeric Le$^x$. The final product can be monitored by positive reaction with monoclonal antibody AH6 defining the Le$^y$ structure (Abe et al., 1983, *J. Biol. Chem.*, 258, 11793-11797) and monoclonal antibody directed to trifucosyl Le$^y$ and extended Le$^y$ (Kaizu et al., 1983, *J. Biol. Chem.*, 261, 11254-11258).

While the invention has been described in detail and with reference to specific embodiments thereof, it will be apparent to one skilled in the art that various changes and modifications can be made therein without departing from the spirit and scope thereof.

What is claimed is:

1. A process for preparing sialyl dimeric Le$^x$ (SA$\alpha$2$\longrightarrow$3Gal$\beta$1$\longrightarrow$4GlcNAc$\beta$1$\longrightarrow$3Gal$\beta$1$\longrightarrow$4Glc$\beta$1$\longrightarrow$1Cer) with a yield of at least

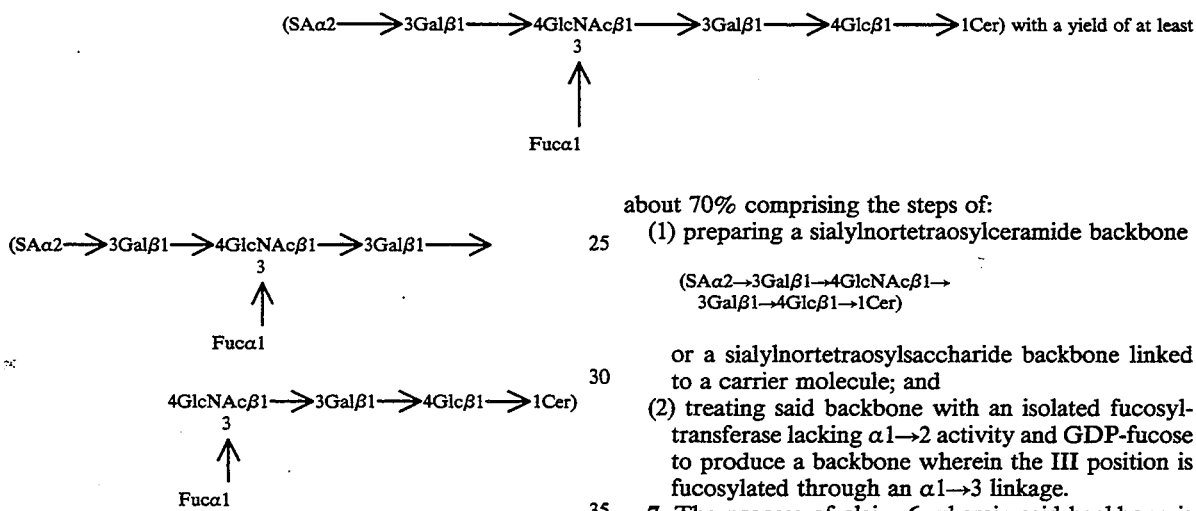

with a yield of at least about 70% comprising the steps of:

(1) preparing a sialylnorhexaosylceramide backbone (SA$\alpha$2$\rightarrow$3Gal$\beta$1$\rightarrow$4GlcNAc$\beta$1$\rightarrow$3Gal$\beta$1$\rightarrow$4GlcNAc$\beta$1$\rightarrow$3Gal$\beta$1$\rightarrow$4Glc$\beta$1$\rightarrow$1Cer)

or a sialylnorhexaosylsaccharide backbone linked to a carrier molecule; and (2) treating said backbone with an isolated fucosyltransferase lacking $\alpha$1$\rightarrow$2 activity and GDP-fucose to produce a backbone wherein the III and V positions are fucosylated through an $\alpha$1$\rightarrow$3 linkage.

2. The process of claim 1 wherein said backbone is synthesized from lactose.

3. The process of claim 1 wherein said backbone is prepared by isolation from a biologic material selected from an organ, tissue or cell.

4. The process of claim 3 wherein said natural source is bovine red blood cells, human placenta or rabbit muscle.

5. The process of claim 1 wherein said step (2) is performed by the $\alpha$1$\rightarrow$3 fucosyltransferase of human colonic adenocarcinoma Colo205.

6. A process for preparing sialyl Le$^x$ (SA$\alpha$2$\rightarrow$3Gal$\beta$1$\rightarrow$4GlcNAc$\beta$1$\rightarrow$3Gal$\beta$1$\rightarrow$4Glc$\beta$1$\rightarrow$1Cer)

about 70% comprising the steps of:

(1) preparing a sialylnortetraosylceramide backbone (SA$\alpha$2$\rightarrow$3Gal$\beta$1$\rightarrow$4GlcNAc$\beta$1$\rightarrow$3Gal$\beta$1$\rightarrow$4Glc$\beta$1$\rightarrow$1Cer)

or a sialylnortetraosylsaccharide backbone linked to a carrier molecule; and (2) treating said backbone with an isolated fucosyltransferase lacking $\alpha$1$\rightarrow$2 activity and GDP-fucose to produce a backbone wherein the III position is fucosylated through an $\alpha$1$\rightarrow$3 linkage.

7. The process of claim 6 wherein said backbone is synthesized from lactose.

8. The process of claim 6 wherein said backbone is prepared by isolation from a biologic material selected from an organ, tissue or cell.

9. The process of claim 8 wherein said natural source is bovine red blood cells, human placenta or rabbit muscle.

10. The process of claim 6 wherein said step (2) is performed by the $\alpha$1$\rightarrow$3 fucosyltransferase of human colonic adenocarcinoma Colo205.

* * * * *

UNITED STATES PATENT AND TRADEMARK OFFICE
CERTIFICATE OF CORRECTION

PATENT NO. : 5,421,733
DATED : June 6, 1995
INVENTOR(S) : Edward Nudelman, et al It is certified that error appears in the above-indentified patent and that said Letters Patent is hereby corrected as shown below:

Col. 3, line 68 delete "numan",
    insert -- human --.

Col. 7, line 8 delete "Sphingolipd",
    insert -- Sphingolipid --.

Signed and Sealed this

Twentieth Day of February, 1996

Attest:

BRUCE LEHMAN

*Attesting Officer*     Commissioner of Patents and Trademarks